(12) United States Patent
Chou et al.

(10) Patent No.: US 11,398,111 B2
(45) Date of Patent: Jul. 26, 2022

(54) INTEGRATED SPECTRUM SENSING DEVICE FOR REAL-FINGER JUDGEMENT AND SENSING METHOD

(71) Applicant: Egis Technology Inc., Taipei (TW)

(72) Inventors: Bruce C. S. Chou, Taipei (TW); Tong-Long Fu, Taipei (TW)

(73) Assignee: EGIS TECHNOLOGY INC., Taipei (TW)

( * ) Notice: Subject to any disclaimer, the term of this patent is extended or adjusted under 35 U.S.C. 154(b) by 0 days.

(21) Appl. No.: 17/141,742

(22) Filed: Jan. 5, 2021

(65) Prior Publication Data

US 2021/0271851 A1    Sep. 2, 2021

Related U.S. Application Data

(60) Provisional application No. 62/983,981, filed on Mar. 2, 2020, provisional application No. 63/029,555, filed on May 24, 2020, provisional application No. 63/031,756, filed on May 29, 2020, provisional application No. 63/036,075, filed on Jun. 8, 2020.

(30) Foreign Application Priority Data

Oct. 30, 2020    (CN) .......................... 202011194826.8

(51) Int. Cl.
*G06V 40/13*    (2022.01)
*G06V 40/12*    (2022.01)
*A61B 5/1455*    (2006.01)

(52) U.S. Cl.
CPC ........ *G06V 40/1388* (2022.01); *A61B 5/1455* (2013.01); *G06V 40/1394* (2022.01); *G06V 40/1341* (2022.01)

(58) Field of Classification Search
CPC ........... G06V 40/1388; G06V 40/1341; G06V 40/1394; A61B 5/1455
See application file for complete search history.

(56) References Cited

U.S. PATENT DOCUMENTS 6,952,489 B1 *  10/2005  Angelo .............. G06V 40/1388
                                                        382/124
9,143,968 B1 *   9/2015  Manku .................. H04W 16/14
(Continued)

FOREIGN PATENT DOCUMENTS

CN    105787420 A    7/2016
CN    108604289 A    9/2018
(Continued)

*Primary Examiner* — Stephen G Sherman
(74) *Attorney, Agent, or Firm* — Muncy, Geissler, Olds & Lowe, P.C.

(57) ABSTRACT

An integrated spectrum sensing device for real-finger judgement includes a fingerprint sensing array, an optical unit and a signal processing unit. The fingerprint sensing array optically coupled to the optical unit includes multiple spectrum detecting units receiving light from a finger through the optical unit to detect spectrum distributions or variations outputted from the finger to obtain multiple sets of heterogeneous spectrum data. The signal processing unit electrically coupled to the spectrum detecting units performs measurement domain analysis according to the sets of heterogeneous spectrum data to judge whether the finger is real. A sensing method is also disclosed.

44 Claims, 21 Drawing Sheets

(56) References Cited

U.S. PATENT DOCUMENTS

| | | | |
|---|---|---|---|
| 9,524,416 B1* | 12/2016 | Rommel | G06V 40/1306 |
| 10,325,142 B2 | 6/2019 | He et al. | |
| 2007/0283428 A1* | 12/2007 | Ma | G06K 19/07354 |
| | | | 714/E11.038 |
| 2008/0037001 A1* | 2/2008 | Yokoyama | G06V 40/67 |
| | | | 356/388 |
| 2009/0046903 A1* | 2/2009 | Corcoran | G06V 10/56 |
| | | | 382/124 |
| 2011/0165911 A1* | 7/2011 | Rowe | G06V 40/1312 |
| | | | 455/556.1 |
| 2014/0286548 A1* | 9/2014 | Shin | G06V 40/1388 |
| | | | 382/127 |
| 2017/0098116 A1 | 4/2017 | Brownlee et al. | |
| 2018/0012056 A1* | 1/2018 | Suwald | G06V 40/1365 |
| 2019/0026527 A1* | 1/2019 | He | G02B 6/0026 |
| 2019/0034020 A1 | 1/2019 | He et al. | |
| 2019/0303639 A1 | 10/2019 | He et al. | |
| 2020/0050818 A1 | 2/2020 | He et al. | |
| 2020/0097696 A1* | 3/2020 | Yao | G06V 40/1318 |

FOREIGN PATENT DOCUMENTS

| | | | |
|---|---|---|---|
| CN | 109643379 A | 4/2019 | |
| CN | 110520863 A | 11/2019 | |
| TW | M491210 U | 12/2014 | |
| TW | M608543 U | 3/2021 | |

\* cited by examiner

INTEGRATED SPECTRUM SENSING DEVICE FOR REAL-FINGER JUDGEMENT AND SENSING METHOD

CROSS-REFERENCE TO RELATED APPLICATIONS

This application claims priorities of U.S. Provisional Patent Application Ser. Nos. 62/983,981, filed on Mar. 2, 2020; 63/029,555, filed on May 24, 2020; 63/031,756, filed on May 29, 2020; and 63/036,075, filed on Jun. 8, 2020; and China Patent Application Ser. No. 202011194826.8, filed on Oct. 30, 2020, the entire contents of which are hereby incorporated by reference.

BACKGROUND OF THE INVENTION

Field of the Invention

This disclosure relates to an integrated spectrum sensing device for real-finger judgement and a sensing method, and more particularly to an integrated spectrum sensing device for real-finger judgement and a sensing method using the physical phenomenon that a finger deforms after pressing so that light reflected by the finger has variations in the time domain, spatial domain and intensity, and the real finger can be judged in conjunction with spectrum detections.

Description of the Related Art

Today's mobile electronic devices (e.g., mobile phones, tablet computers, notebook computers and the like) are usually equipped with user biometrics recognition systems including different techniques relating to, for example, fingerprint, face, iris and the like, to protect security of personal data. Portable devices applied to mobile phones, smart watches and the like also have the mobile payment function, which further becomes a standard function for the user's biometrics recognition. The portable device, such as the mobile phone and the like, is further developed toward the full-display (or super-narrow border) trend, so that conventional capacitive fingerprint buttons can no longer be used, and new minimized optical imaging devices, some of which are very similar to the conventional camera module having complementary metal-oxide semiconductor (CMOS) image sensor (referred to as CIS) sensing members and an optical lens module, are thus evolved. The minimized optical imaging device is disposed under the display as an under-display device. The image of the object (more particularly the fingerprint) placed above the display can be captured through the partial light-permeable display (more particularly the organic light emitting diode (OLED) display), and this can be called as fingerprint on display (FOD).

The FOD sensing needs to correctly sense the fingerprint, and also to judge whether the finger is real to prevent someone from passing through the authentication using the fake fingerprint or finger. At present, the spoofing technology is getting more and more refined. For example, a mold may be made from a 2D image or by 3D printing, and the mold is filled with various silica gels and pigments to produce the fake finger. Alternatively, another person's fingerprint may be copied into a transparent or skin-color film attached to the finger surface, so that the fake finger attached with the transparent film cannot be easily distinguished. Special attentions needs to be paid on this fake finger recognition technology upon the FOD sensing because the display may shield partial characteristics of the finger to affect the recognition result.

According to the above-mentioned descriptions, the mechanism and method for judging the real finger need to be further improved to prevent the fake finger from passing through the fingerprint recognition.

BRIEF SUMMARY OF THE INVENTION

It is therefore an object of this disclosure to provide an integrated spectrum sensing device for real-finger judgement and a sensing method capable of judging the real finger, wherein the physical phenomenon that the finger deforms after pressing are used in conjunction with different spectrum detections in the time and/or spatial domains to judge whether the finger is real.

Another object of this disclosure is to provide an integrated spectrum sensing device for real-finger judgement and a sensing method capable of judging the real finger, wherein neighboring light sensing cells are used in conjunction with different spectrum separating cells to obtain different intensities, and the real finger is judged according to one or multiple ratios of these intensities.

To achieve the above-identified objects, this disclosure provides an integrated spectrum sensing device including: an optical unit; a fingerprint sensing array being optically coupled to the optical unit and including multiple spectrum detecting units receiving light from a finger through the optical unit to detect spectrum distributions or variations outputted from the finger to obtain multiple sets of heterogeneous spectrum data; and a signal processing unit, which is electrically coupled to the spectrum detecting units, and performs measurement domain analysis according to the sets of heterogeneous spectrum data to judge whether the finger is real.

This disclosure also provides an integrated real-finger spectrum sensing method including steps of: (a) using multiple spectrum detecting units of a fingerprint sensing array to sense spectrum distributions or variations outputted from a finger through an optical unit to obtain multiple sets of heterogeneous spectrum data, wherein the optical unit is optically coupled to the spectrum detecting units; and (b) performing measurement domain analysis according to the sets of heterogeneous spectrum data to judge whether the finger is real.

With the above-mentioned embodiments, it is possible to utilize the physical phenomenon that the finger deforms after pressing in conjunction with spectrum detection to judge whether the finger is real. On the other hand, the real finger can be effectively and correctly judged according to the spectrum verification in the time and/or spatial domains. The hardware, firmware or software can be utilized to perform the spectrum verification in the time and/or spatial domains to avoid the security problem that the fake finger passes the verification. In addition, neighboring light sensing cells are used in conjunction with different spectrum separating cells to obtain different intensities, and whether the finger is real is judged according to one or multiple ratios of these intensities. The simple optical coating treatment for the spectrum separating cells is utilized so that the manufacturing cost needs not to be significantly increased and that the anti-spoofing detection of the finger can be achieved. Also, the problem that the interested party intends to pass fingerprint verification using the fake finger can be effectively solved.

Further scope of the applicability of this disclosure will become apparent from the detailed description given here-

DETAILED DESCRIPTION OF THE INVENTION

This disclosure is mainly achieved according to the non-uniform capillary distribution contained in the real finger. Thus, the finger's nonuniform color distribution in the geometric space can be normally seen. In addition, when the finger starts to touch a surface (e.g., the display surface of the mobile phone), under which a FOD sensor is disposed, the capillaries in the finger are pressed to obstruct the blood flow, and the finger's skin color is further changed, so color variations on the time axis are generated. According to one or both of the two phenomena, the property of the real finger can be judged as either true or false, and the fake finger's attack can be thus avoided. On the other hand, the embodiment is achieved mainly by the conventional CIS RGB pixels (the prior art utilizes all or almost all the RGB pixels), which can measure the full-color spectrums. In one optical fingerprint sensing array (the prior art utilizes all white pixels to receive all visible light spectrums or some infrared spectrums), some of the pixels are configured into pseudo CIS RGB pixels distributed in the array to obtain the spectrum variations on the finger surface in the spatial domain and time domain.

Figure 1:
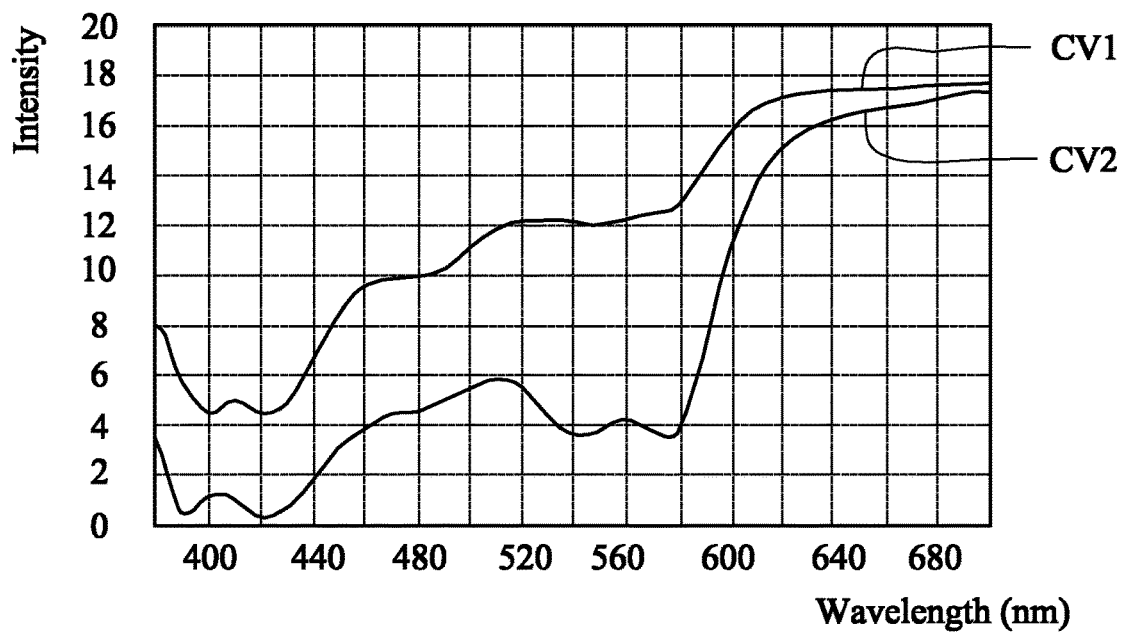
FIG. 1 is a spectrum chart showing a finger in conditions with and without pressures.

FIG. 1 is a spectrum chart showing a finger in conditions with and without pressures. It is noted that this experiment may vary from person to person, and only shows its property without quantifying the data. Referring to FIG. 1, the horizontal axis denotes the wavelength, the vertical axis denotes the intensity, and curves CV1 and CV2 respectively denote the spectrum properties of the finger's certain portion in conditions with and without pressures. For example, according to the intensity level variations for the wavelengths ranging from 380 nm to 580 nm, it is obtained that the finger's spectrums with and without pressures can reach the predetermined levels. Whether the sensed finger is real can be determined according to multiple sets of training data. This is a dynamic sensing method for sensing the pressure variations of the finger's initial, middle and late pressing stages, in which different spectrum intensity information are presented. In one embodiment, however, the optimum solution can be obtained by machine learning or artificial intelligence (AI) algorithms. In one example, the algorithm of analyzing the color spectrum may include: collecting color spectrum information from different materials, fingers and/or light conditions; and then building an analysis system and algorithm to distinguish real fingers from fake fingers. In another example, an AI neural network (NN) scoring may be adopted to: get the image of the fingerprint from the sensor; and test the fingerprint image through the AI model to get the fake/real fingerprint confidence. The algorithm of analyzing the color spectrum may be combined with the AI NN scoring to decide the result of the real/fake finger.

Figure 2:
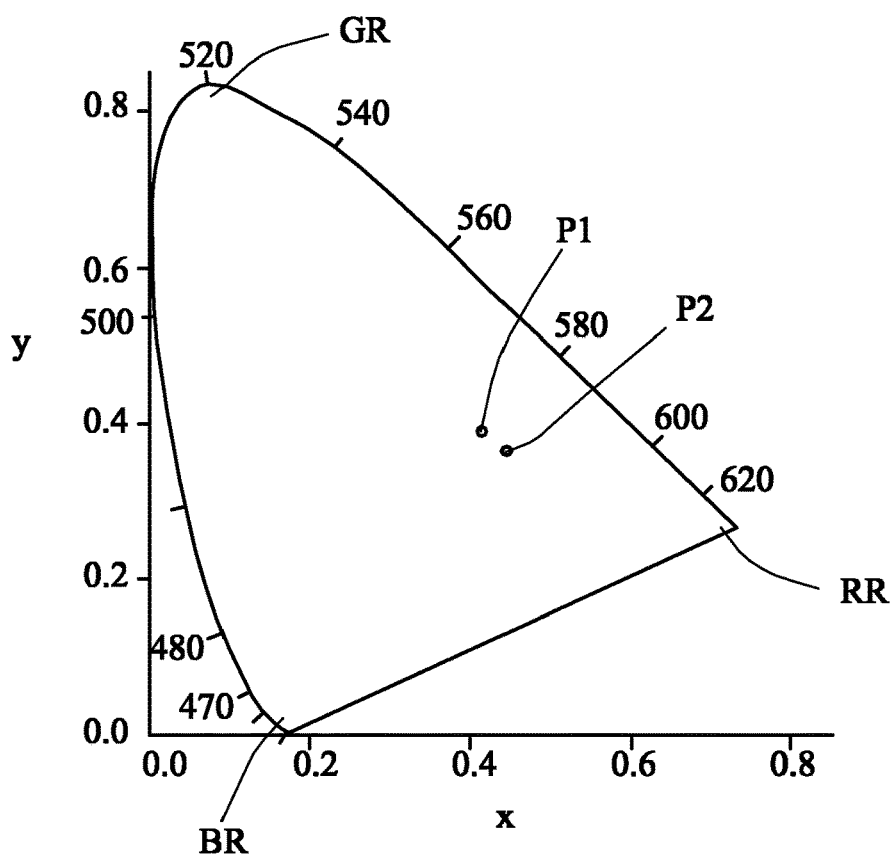
FIG. 2 is a schematic view showing the chart of FIG. 1 transformed into the CIE 1931 color space.

FIG. 2 is a schematic view showing the chart of FIG. 1 transformed into the CIE 1931 color space. As shown in the CIE 1931 color space of FIG. 2, the corner RR is red, the corner GR is green, and the corner BR is blue. The point P1 corresponds to the curve CV1 and thus the finger with pressure. The point P2 corresponds to the curve CV2 and thus the finger without pressure. If "L" is used to describe the brightness value (ranging from 0 to 100), "a" is used to describe the green-to-magenta value (ranging from −500 to 500), and "b" is used to describe the blue-to-yellow value (ranging from −200 to 200), then the point P1 has (L, a, b) as (39.94, 9.26 and 16.79); and the point P2 has (L, a, b) as (27.73, 21.16 and 17.96). It is observed that the sensed spectrum is reddish when the finger is not pressed, and is less reddish when the finger is pressed. The main reason is that when the finger is pressed, the blood flow of the capillary will be blocked, so that the sensed spectrum is less reddish. Thus, the optimum solution serving as the useful database to assist in judging the real finger can be obtained according to a lot of training data at the points P1 and P2, the machine learning, and/or the artificial intelligence algorithm.

Figure 3A:
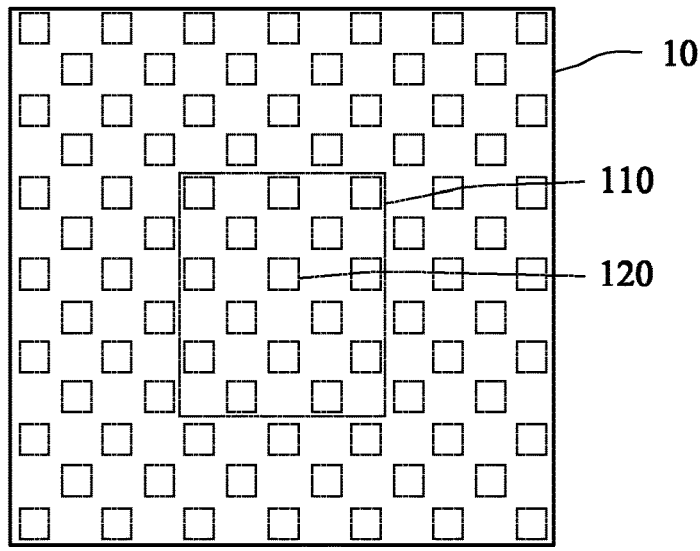
FIG. 3A is a schematic partial plane view showing an integrated spectrum sensing device according to a preferred embodiment of this disclosure.
Figure 3B:
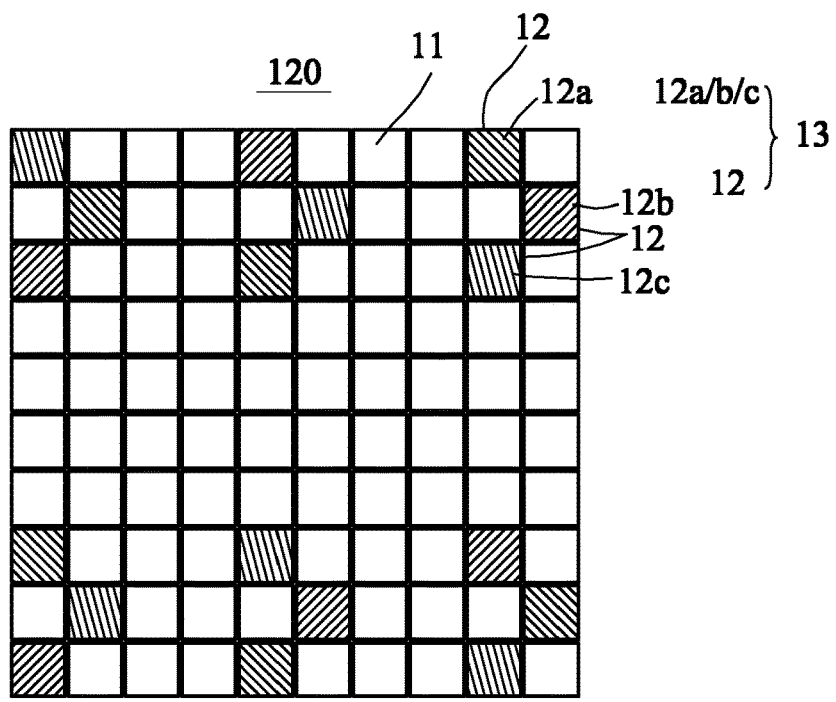
FIG. 3B is a schematic enlarged view showing a second block of FIG. 3A.

FIG. 3A is a schematic partial plane view showing an integrated spectrum sensing device according to a preferred embodiment of this disclosure. FIG. 3B is a schematic enlarged view showing a second block of FIG. 3A. Referring to FIGS. 3A and 3B, the integrated spectrum sensing device (ISSD) 100 includes light sensing cells 11 and spectrum sensing cells 12 (similar to the RGB pixels of CIS) arranged in a two-dimensional array. Some light sensing cells 11 and some spectrum sensing cells 12 constitute a spectrum cluster block 120. Multiple spectrum cluster blocks 120 constitute a sensing region 110, which may be referred to as a region of interest (ROI). Other light sensing cells 11 may also be arranged at positions between the spectrum cluster blocks 120. Although the light sensing cells 11 and the spectrum sensing cells 12 are not depicted in FIG. 3A, a fingerprint sensing array 10 may be defined according to the light sensing cells 11 and spectrum sensing cells 12 of FIG. 3B. In the spectrum cluster block 120, heterogeneous spectrum separating cells 12*a*, 12*b* and 12*c* (e.g., blue (B), green (G) and red (R) spectrum separating cells) cover some of the spectrum sensing cells 12, while no spectrum separating cell covers the other light sensing cells 11. Herein, the heterogeneous spectrum separating cells 12*a*, 12*b* and 12*c* denote the narrow spectrums (e.g., conventional RGB colors) that can correspond to the spectrum separating cells 12*a*, 12*b* and 12*c*. Thus, three spectrum sensing cells 12 and the heterogeneous spectrum separating cells 12*a*, 12*b* and 12*c* constitute one spectrum detecting unit 13 in this example, and the spectrum sensing cells 12 can detect the full visible light spectrum through the heterogeneous spectrum separating cells 12*a*, 12*b* and 12*c* of three primary colors (RGB). The ISSD 100 can obtain the data of each spectrum cluster and has the hardware for calculating and storing the information of the spectrum detecting unit into the sensor's register or storage area, any internal or external module or the systems random access memory (RAM) or special memory, such as the volatile or non-volatile memory including the one-time programmable (OTP) memory, multiple-time programmable (MTP) memory, electrically-erasable programmable read-only memory (EEPROM) and the like. The information of the spectrum detecting unit 13 may include the full spectrum (RGB or RGBW) information (W represents the black-and-white). Properly arranging the spectrum detecting units can obtain the finger's correct local information. Of course, each spectrum detecting unit 13 is constituted by three spectrum sensing cells 12 and three heterogeneous spectrum separating cells 12*a*, 12*b* and 12*c* of three primary-colors in this preferred embodiment. In other embodiments, one spectrum sensing cell 12 can be used in conjunction with one heterogeneous spectrum separating cell 12*a* or 12*b* or 12*c*, or any two spectrum sensing cells 12 may be used in conjunction with two heterogeneous spectrum separating cells to constitute one spectrum detecting unit 13. Thus, according to another definition, one spectrum sensing cell 12 and one heterogeneous spectrum separating cell 12*a* may also constitute the spectrum detecting unit. In this case, the heterogeneous spectrum separating cell is only the definition of the term, and may also be referred to as the spectrum separating cell.

Figure 3C:
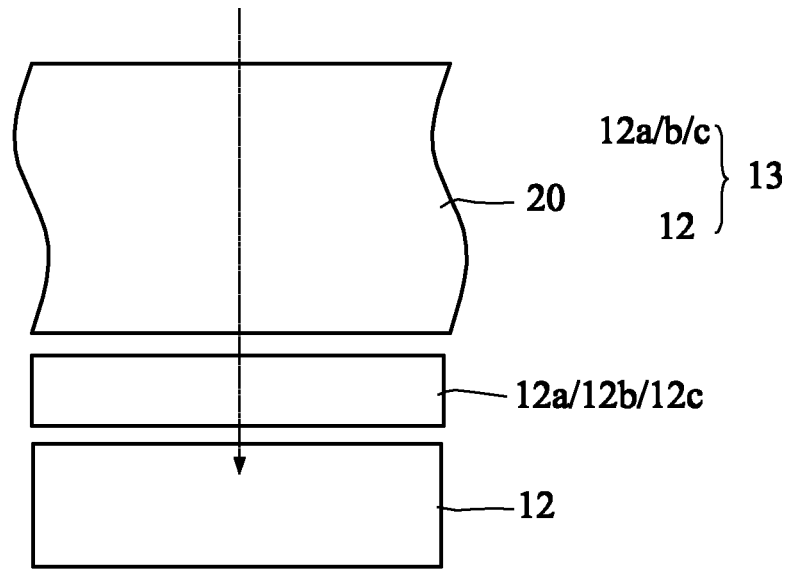
FIGS. 3C and 3D are schematic views showing two examples of spectrum detecting units working in conjunction with optical units.
Figure 3D:
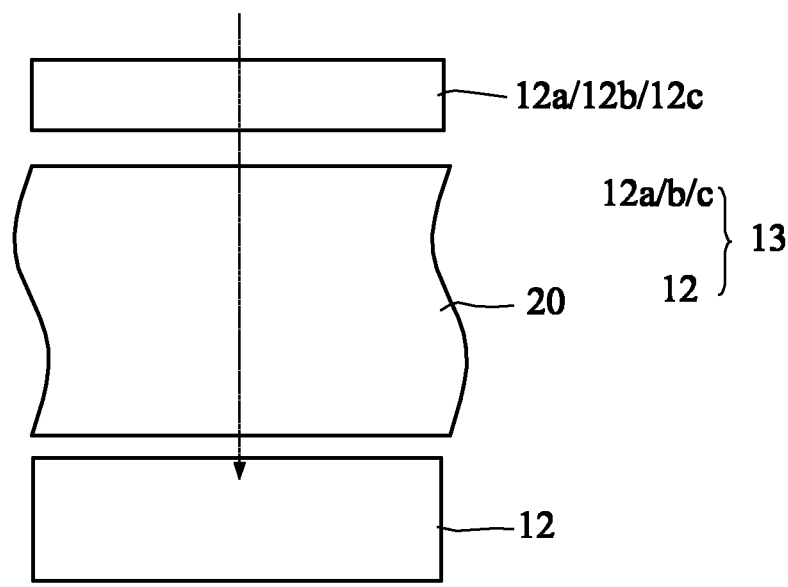

FIGS. 3C and 3D are schematic views showing two examples of spectrum detecting units 13 working in conjunction with optical units 20. Referring to FIG. 3C, the spectrum detecting unit 13 of the fingerprint sensing array 10 is constituted by the spectrum sensing cells 12 and the spectrum separating cells 12*a*, 12*b* and 12*c*. The spectrum detecting unit 13 works in conjunction with one portion (e.g., the conventional lens) or the whole portion (e.g., micro-lenses) of the optical unit 20 to achieve the spectrum detecting effect. According to another definition, a corresponding portion of the optical unit 20 may also be incorporated into the fingerprint sensing array, but this disclosure is not limited thereto. The optical unit 20 may include structures, such as micro-lenses and light apertures, or may also be an optical collimator (an optical channel collimator, such as an optical fiber board, one of other types of structures with the same function, an angle collimator constituted by micro-lenses and light apertures, and the like). Alternatively, the optical unit 20 may also be a conventional refraction, diffraction or reflection lens set. It is worth noting that the arrangements of FIGS. 3C and 3D are only provided to schematically explain the relative relationships between cells/elements without restricting the manufacturing process relationships therebetween or implying a complete direct contact therebetween. In FIG. 3C, the optical unit 20 is disposed on or above the heterogeneous spectrum separating cells 12*a*/12*b*/12*c*, which are disposed between the spectrum sensing cells 12 and the optical unit 20. The spectrum sensing cells 12 receive the spectrum distributions outputted from the finger through the optical unit 20 and the spectrum separating cells 12*a*/12*b*/12*c*. In FIG. 3D, the optical unit 20 is disposed between the spectrum sensing cells 12 and the heterogeneous spectrum separating cells 12*a*, 12*b* and 12*c*, the spectrum separating cells 12*a*/12*b*/12*c* are disposed on or above the optical unit 20, and the spectrum sensing cells 12 receive the finger's spectrums through the spectrum separating cells 12*a*/12*b*/12*c* and the optical unit 20. According to FIGS. 3B to 3D, it is obtained that the optical unit 20 can be disposed in or above the spectrum detecting units 13 as long as the optical unit 20 can be optically coupled to the spectrum detecting units 13 to achieve the spectrum detection and optical sensing effects.

Figure 4:
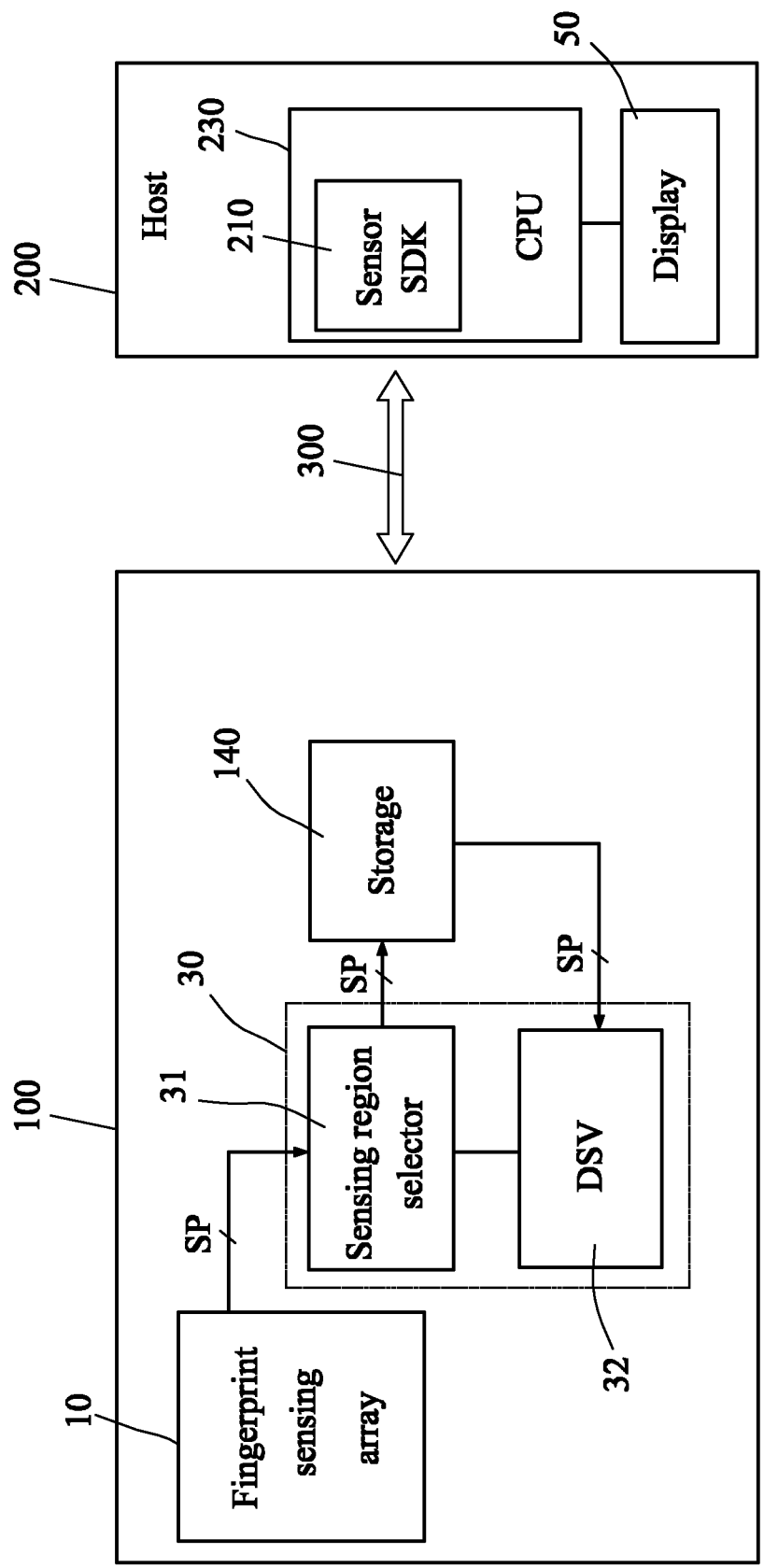
FIG. 4 is a schematic operational view showing the integrated spectrum sensing device and a host.

FIG. 4 is a schematic operational view showing the ISSD 100 and a host 200. Referring to FIGS. 4 and 3A to 3D, this embodiment provides the ISSD 100 including the optical unit 20, the fingerprint sensing array 10 and a signal processing unit 30. The fingerprint sensing array 10 optically coupled to the optical unit 20 includes spectrum detecting units 13 for receiving light from a finger to detect spectrum distributions or variations outputted from the finger through the optical unit 20 to obtain multiple sets of heterogeneous spectrum data SP. In one non-restrictive example, white light illuminates the finger. The fingerprint sensing array 10 may further include light sensing cells 11. The spectrum detecting units 13 include spectrum sensing cells 12, and neighboring heterogeneous spectrum separating cells 12*a*, 12*b* and 12*c*, which cover the spectrum sensing cells 12 and may be arranged in a diagonal neighboring and staggered manner, so that the spectrum sensing cells 12 corresponding to the heterogeneous spectrum separating cells 12*a*, 12*b* and 12*c* sense the finger through the optical unit 20 and the heterogeneous spectrum separating cells 12*a*, 12*b* and 12*c*. In one example, the light sensing cell 11 and the spectrum sensing cell 12 have the same structure and property to decrease the manufacturing cost. In one example, the light sensing cell 11 and the spectrum sensing cell 12 may be configured to have different properties (e.g., sensitivities). For example, the spectrum sensing cell 12 has the high sensitivity to provide the more accurate real-finger judgement result. In addition, the ISSD 100 shown in FIG. 4 is electrically coupled (or connected) to the host 200 having a display 50. The host 200 can be the mobile phone, tablet computer, desktop computer, notebook computer and the like, wherein the associated configuration of the ISSD 100 and the host 200 has been described in FIGS. 11 to 13. The display 50 can display information to interact with the user, and may also provide light to illuminate the finger, which then generates reflected light or transmitted/refracted light (entering the finger and then be transmitted/refracted out). Of course, an additional light source may also be provided to illuminate the finger. The display 50 may also have the touch function and provide a touch event signal to the ISSD 100. Thus, the signal processing unit 30 is electrically coupled to a central processing unit (CPU) 230 of the host 200. The CPU 230 is electrically coupled to the display 50 of the host 200, and controls operations of the display 50 and the signal processing unit 30. In this condition, the ISSD 100 has the independent signal processing unit capable of directly judging the real finger and decreasing the complexity of matching with the host 200.

In addition, because the heterogeneous spectrum separating cells 12a, 12b and 12c are concurrently present in this example, the mixed spectrum of light may be adopted as the light source providing light to the finger, so that the fingerprint sensing array 10 can obtain multiple sets of heterogeneous spectrum data SP at a time. The sets of heterogeneous spectrum data SP may be stored in a storage 140 electrically coupled to the fingerprint sensing array 10 and signal processing unit 30. The signal processing unit 30 is electrically coupled to the spectrum sensing cells 12, and performs measurement domain analysis according to the sets of heterogeneous spectrum data SP to judge whether the finger is real. For example, the spectrum variations of the sets of heterogeneous spectrum data SP in one or both of a time domain and a spatial domain are analyzed to judge whether the finger is real. Herein, measurement domain analysis includes time domain analysis and/or spatial domain analysis. The ISSD 100 is applicable to the under-display or other independent occasion, and is not particularly restricted.

The light sensing cells 11 not covered by the heterogeneous spectrum separating cells sense the finger's fingerprint through the optical unit 20 to obtain a fingerprint image. Of course, the signals obtained by the light sensing cells 11 and the spectrum sensing cells 12 may also be integrated into the fingerprint image.

In this example, the signal processing unit 30 may include a sensing region selector 31 and a dynamic spectrum verifier (DSV) 32. The sensing region selector 31 electrically coupled to the fingerprint sensing array 10 selects a sensing region 110 (or ROI) of the fingerprint sensing array 10 according to a touch event signal to enable the fingerprint sensing array 10 to generate the sets of heterogeneous spectrum data SP corresponding to the sensing region 110. The touch event signal may come from a touch panel (not shown) above the fingerprint sensing array 10. In one example, the sensing region selector 31 provides a spectrum cluster ROI selecting function for selecting the ROI's spectrum cluster information, and then calculating the finger spectrum distributions or variations, and storing the values into the storage 140. The DSV 32 detects the spectrum cluster information in the time domain and calculates the spectrum variation parameters. Thus, the DSV 32 is in charge of analyzing the spectrum variations of the sets of heterogeneous spectrum data SP in the time domain to judge the real finger. The host 200 connected to the ISSD 100 through a wired or a wireless connection interface 300 can directly acquire the recognition result of the DSV 32, and also acquire the heterogeneous spectrum data SP from the storage 140 through a sensor software development kit (SDK) 210 executing in the CPU 230 to perform the further verification the same as or different from that of the DSV 32. In another example, the ISSD 100 may have no DSV 32 and directly perform the dynamic spectrum verification through the sensor SDK 210.

Figure 5:
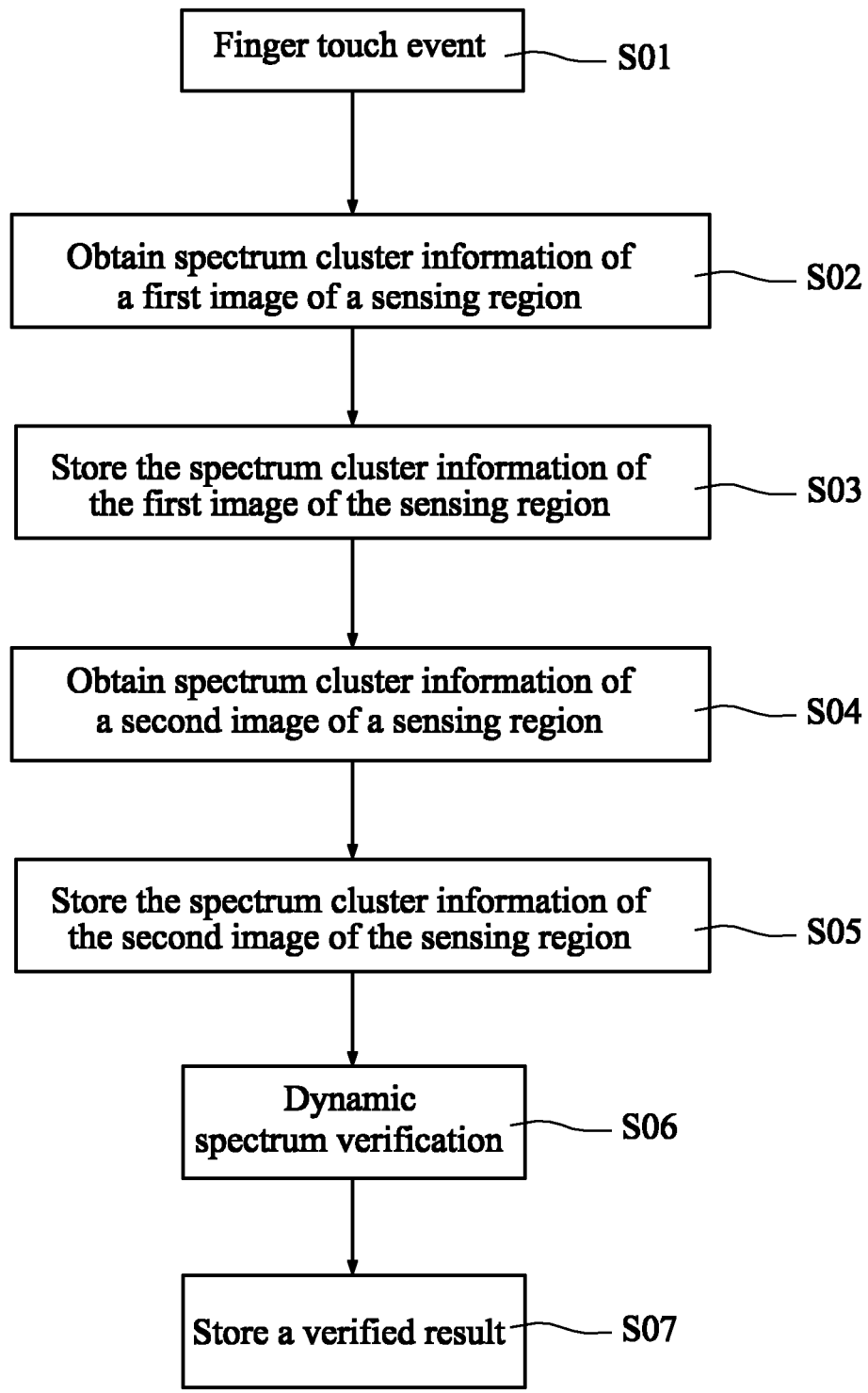
FIG. 5 is a flow chart showing one example of an integrated spectrum sensing method.

FIG. 5 is a flow chart showing one example of an integrated spectrum sensing method. Referring to FIG. 5, a finger touch event is detected, and a sensing region is selected according to the touch event signal in step S01. Next, in step S02, the fingerprint sensing array 10 obtains the spectrum cluster information of the first image of the sensing region. That is, the fingerprint sensing array 10 senses the sensing region 110 at a first time to obtain a first set of heterogeneous spectrum data SP. Then, in step S03, the spectrum cluster information of the first image of the sensing region (i.e., the first set of heterogeneous spectrum data SP) is stored. Next, in step S04, the fingerprint sensing array 10 obtains the spectrum cluster information of the second image of the sensing region. That is, the fingerprint sensing array 10 senses the sensing region 110 at a second time to obtain a second set of heterogeneous spectrum data SP. Then, in step S05, the spectrum cluster information of the second image of the sensing region (i.e., the second set of heterogeneous spectrum data SP) is stored. Then, in step S06, the dynamic spectrum verification is performed. That is, the signal processing unit 30 analyzes the spectrum variations of the sets of heterogeneous spectrum data SP at the first time and the second time to judge the real finger. Finally, in step S07, the verified result is stored.

Thus, this embodiment provides an integrated real-finger spectrum sensing method, which may be summarized, in conjunction with FIGS. 5 and 4, to include the following steps. Optionally, as shown in step S01, the touch event signal is received, and the sensing region 110 of the fingerprint sensing array 10 is selected according to the touch event signal to enable the fingerprint sensing array 10 to generate the sets of heterogeneous spectrum data SP corresponding to the sensing region 110. Then, as shown in steps S02 to S05, the spectrum detecting units 13 of the fingerprint sensing array 10 (constituted by the heterogeneous spectrum separating cells 12a, 12b and 12c and the spectrum sensing cells 12) are utilized to sense the spectrum distributions or variations outputted from the finger (i.e., the spectrum distributions or variations of light outputted from the finger and carrying fingerprint information) to obtain multiple sets of heterogeneous spectrum data SP. Next, as shown in steps S06 to S07, the spectrum variations of the sets of heterogeneous spectrum data SP in one or both of the time domain and spatial domain are analyzed to judge the real finger, and the verified result is stored. When the spectrum variations in the time domain are sensed, the first image of step S02 and the second image of step S04 may respectively represent global images at different times. When the spectrum variations in the spatial domain are sensed, the first image of step S02 and the second image of step S04 may respectively represent local images obtained at different positions in the same time period.

Figure 6:
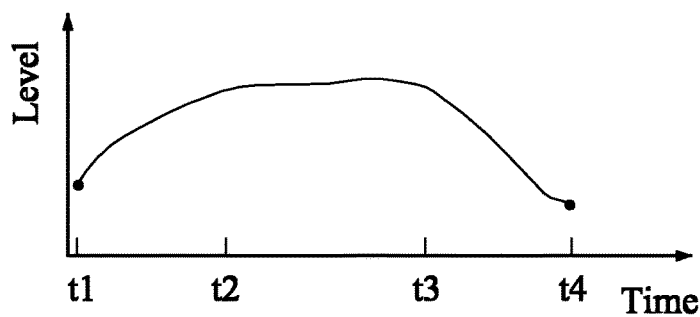
FIG. 6 is a schematic view showing a finger touch event.

FIG. 6 is a schematic view showing the finger touch event. In FIG. 6, the horizontal axis denotes the time, and the vertical axis denotes the level corresponding to the touch force. As shown in FIG. 6, the time point t1 indicates that the touch panel senses a finger touch, the time point t4 indicates that the finger leaves the touch panel, and the period from the time point t2 to the time point t3 indicates that the finger is stably touching the touch panel. Thus, the first time may be the starting period (t1 to t2) or ending period (t3 to t4) of the touch event, and the second time may be the middle period (t2 to t3) of the touch event. Thus, a first pressure of the finger directly or indirectly contacting the fingerprint sensing array 10 at the first time is lower than a second pressure of the finger directly or indirectly contacting the fingerprint sensing array 10 at the second time. The human finger's touch behavior may function as the training data, and the first time and the second time can be properly selected to provide the basis for the real-finger judgement.

Figure 7:
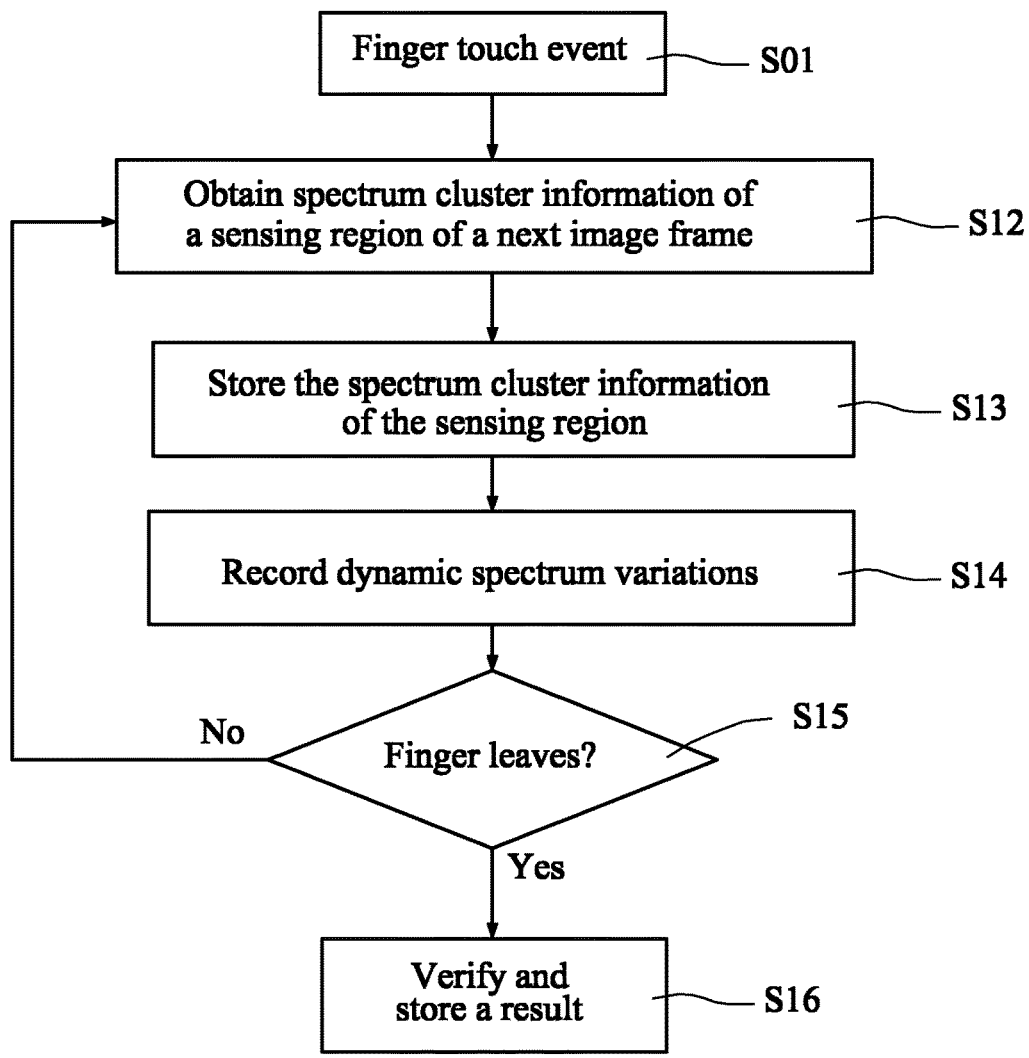
FIG. 7 is a flow chart showing another example of the integrated spectrum sensing method.

FIG. 7 is a flow chart showing another example of the integrated spectrum sensing method. In FIGS. 7 and 6, the spectrum cluster information (heterogeneous spectrum data SP) may also be dynamically captured and stored in the period when the finger touch event is present. After the touch event disappeared, the dynamic spectrum verification can be performed according to the stored spectrum cluster information. Step S01 in FIG. 7 is the same as that in FIG. 5. After step S01, the spectrum cluster information of the sensing region of the next image frame is obtained (step S12), and then stored (step S13). Next, the dynamic spectrum variations are recorded (step S14), wherein the dynamic spectrum verification can be performed and the verified result can be recorded into the storage. Then, whether the finger leaves is detected (step S15). If the finger does not leave, then steps S12 to 14 are repeated. If the finger has left, then an optional step S16 is performed to verify and store the result. This step S16 can be performed at the end of the host, and may also be performed by the hardware circuit additionally provided in the ISSD.

It is worth noting that in addition to analyzing the spectrum variations of the sets of heterogeneous spectrum data SP in one or both of the time domain and spatial domain, the signal processing unit 30 may also perform comparison according to the ratio(s) or mathematical operation result(s) of the neighboring heterogeneous spectrum data SP of the same frame to assist the real-finger judgement. That is, the intensity domain analysis pertaining to the measurement domain analysis may also be performed.

In FIGS. 4 and 1, the signal processing unit 30 can analyze whether the level variations of the sets of heterogeneous spectrum data SP at the wavelength ranging from 380 nm to 580 nm reach a predetermined level (e.g., the average level difference between the curves CV1 and CV2) to perform the real-finger judgement. In FIGS. 4 and 2, the signal processing unit 30 can analyze whether the position variations of the sets of heterogeneous spectrum data SP in the CIE 1931 color space reach a predetermined offset (e.g., the average offset from points P1 to P2, and the offset can be obtained according to the training data) to perform the real-finger judgement.

Figure 8A:
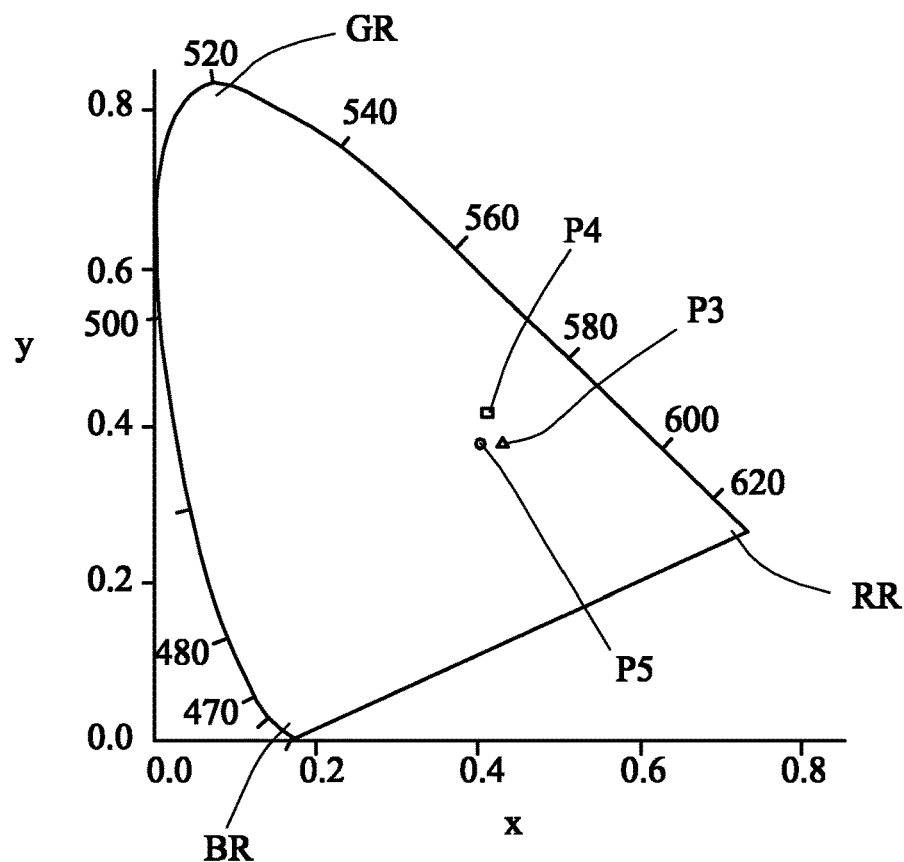
FIG. 8A is a distribution chart showing the spatial-domain finger spectrum chart in the CIE 1931 color space.
Figure 8B:
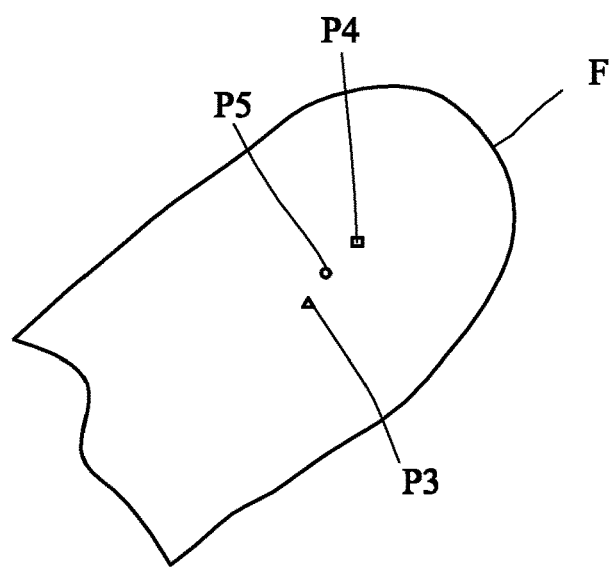
FIG. 8B is a distribution chart showing multiple points corresponding to FIG. 8A on the finger.

FIG. 8A is a distribution chart showing the spatial-domain finger spectrum chart in the CIE 1931 color space. FIG. 8B is a distribution chart showing multiple points corresponding to FIG. 8A on the finger. That is, the spectrums outputted from three points P3, P4 and P5 on the finger F sensed by the ISSD 100 in the CIE 1931 color space are located at positions of FIG. 8A. The finger's spectrum variations in the spatial domain are present because the finger's tiny blood vessels are under the nonuniform pressure. At present, no fake finger is found to have such the phenomena. That is, the spectrums correspondingly outputted from two different points on the real finger have difference under the nonuniform pressure, and the difference can be found in the CIE 1931 color space. The spectrums corresponding to two different points of the pressed fake finger has no difference. That is, the positions of the three points P3, P4 and P5 in the CIE 1931 color space are overlapped for the fake finger. It is worth noting that although three points are explained, examples having two points or more than four points may also be used upon actual implementation.

The real-finger judgement can be performed using the architecture of FIG. 4 in conjunction with the spatial domain variations. Referring to FIGS. 3A, 4, 8A and 8B, the fingerprint sensing array 10 senses different positions of the sensing region 110 (e.g., the points P3, P4 and P5 corresponding to FIG. 8B) to obtain the sets of heterogeneous spectrum data SP (e.g., three sets of heterogeneous spectrum data corresponding to the points P3, P4 and P5 of FIG. 8A), and the signal processing unit 30 analyzes spectrum variations of the sets of heterogeneous spectrum data SP at different positions. At this time, the DSV 32 can provide the spatial spectrum verifying function. On the other hand, the signal processing unit 30 analyzes whether the position variations of the sets of heterogeneous spectrum data SP in the CIE 1931 color space reach a predetermined offset to perform the real-finger judgement.

The double verification may also be performed according to the time domain variations and spatial domain variations of the sets of heterogeneous spectrum data SP, so that the judged result becomes more accurate. In this condition, the fingerprint sensing array 10 senses the sensing region 110 to obtain multiple sets of heterogeneous spectrum data SP at the first time and the second time, and the signal processing unit 30 analyzes the spectrum variations of the sets of heterogeneous spectrum data SP at the first time and the second time to perform the real-finger judgement. In addition, the signal processing unit 30 analyzes the spectrum variations of the sets of heterogeneous spectrum data SP corresponding to one or both of the first time and the second time at different positions to perform the further real-finger judgement.

Figure 9:
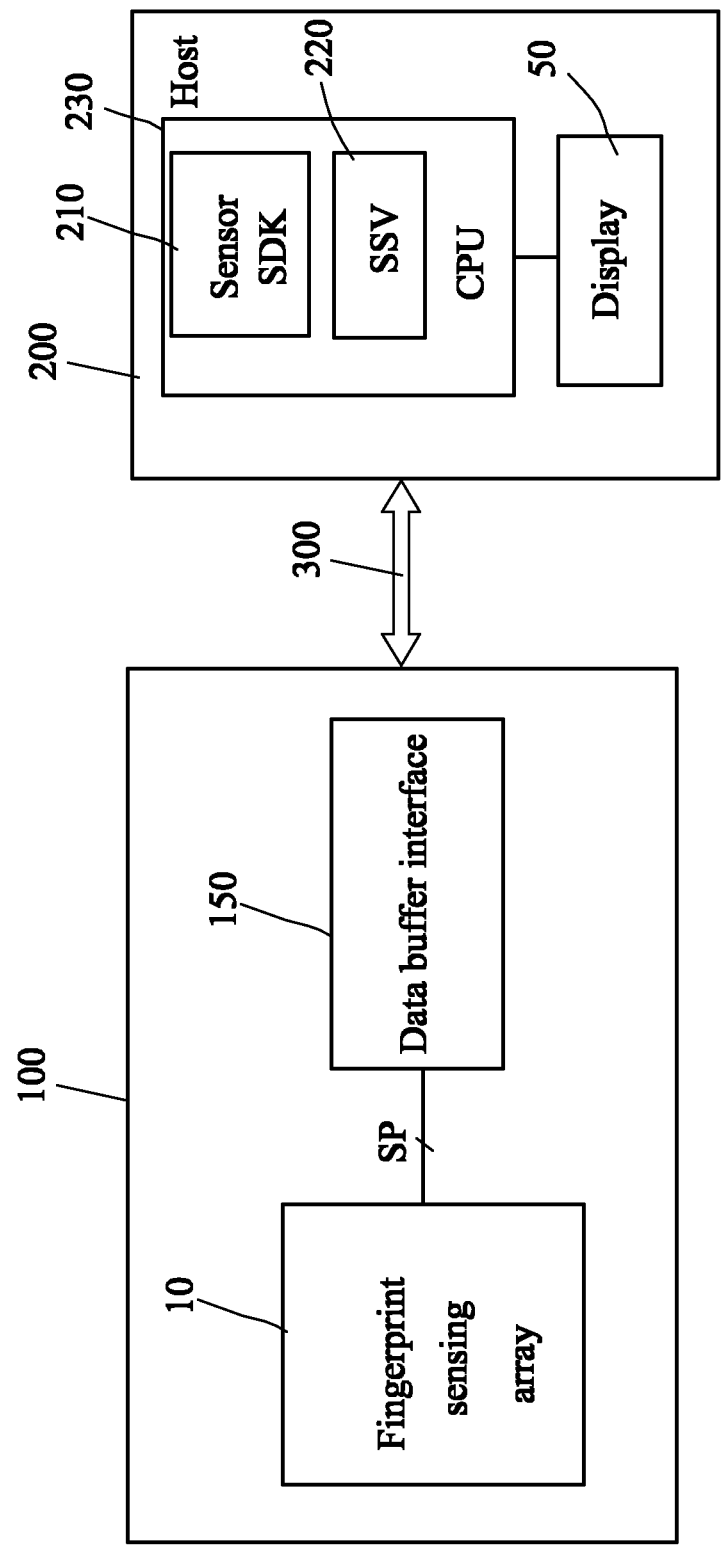
FIG. 9 is one block diagram showing a hardware device for implementing the spectrum variation judgement in the spatial domain.

FIG. 9 is one block diagram showing a hardware device for implementing the spectrum variation judgement in the spatial domain. In FIG. 9 (similar to FIG. 4), the fingerprint sensing array 10 of the ISSD 100 senses different positions of the sensing region to obtain multiple sets of heterogeneous spectrum data SP, which are transmitted to the host 200 through a data buffer interface 150 and the connection interface 300. The sensor SDK 210 executing in the CPU 230 of the host 200 works in conjunction with a spatial spectrum verifier (SSV) 220 and the artificial intelligent engine for fingerprint to perform the spatial spectrum verifying function and the other functions mentioned hereinabove.

Figure 10:
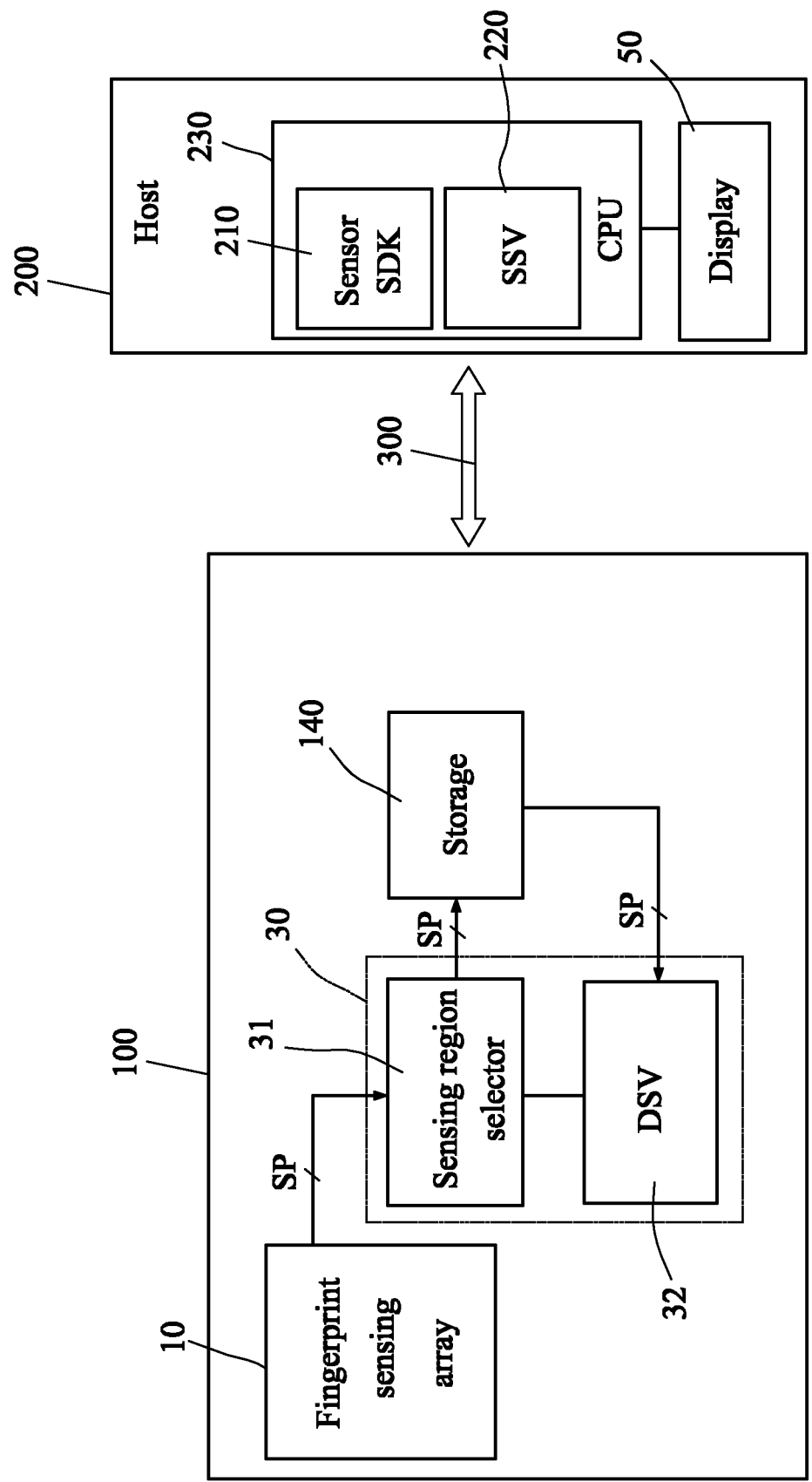
FIG. 10 is another block diagram showing the hardware device for implementing the spectrum variation judgement in the spatial domain.

FIG. 10 is another block diagram showing the hardware device for implementing the spectrum variation judgement in the spatial domain. In FIG. 10, this example is made by combining the configurations of FIGS. 4 and 9, wherein the time domain processing of dynamic spectrum verification can be performed in the DSV 32 of the ISSD 100, and the spatial spectrum verification processing can be performed in the SSV 220 of the host 200. However, this is only one of examples without limiting this disclosure thereto. In addition, although the CIE 1931 color space functions as a descriptive example, the concept of this disclosure may also be applied to the existing or future color space to judge whether the finger is real.

With the above-mentioned embodiments, it is possible to utilize the physical phenomenon that the finger deforms after pressing in conjunction with spectrum detection to judge whether the finger is real. On the other hand, the real finger can be effectively and correctly judged according to the spectrum verification in the time domain and/or spatial domain. The hardware, firmware or software can be utilized to perform the spectrum verification in the time domain and/or spatial domain to avoid the security problem that the fake finger passes the verification.

The above-mentioned judging method can achieve the effect of judging the real finger. That is, the to-be-detected finger is judged as either a real finger or not (the judged result is "either true or false"). As long as the real-finger conditions cannot be satisfied, the finger is judged as fake. There is no mis-judgement for some realistic fingers having properties very similar to the real finger.

Figure 11:
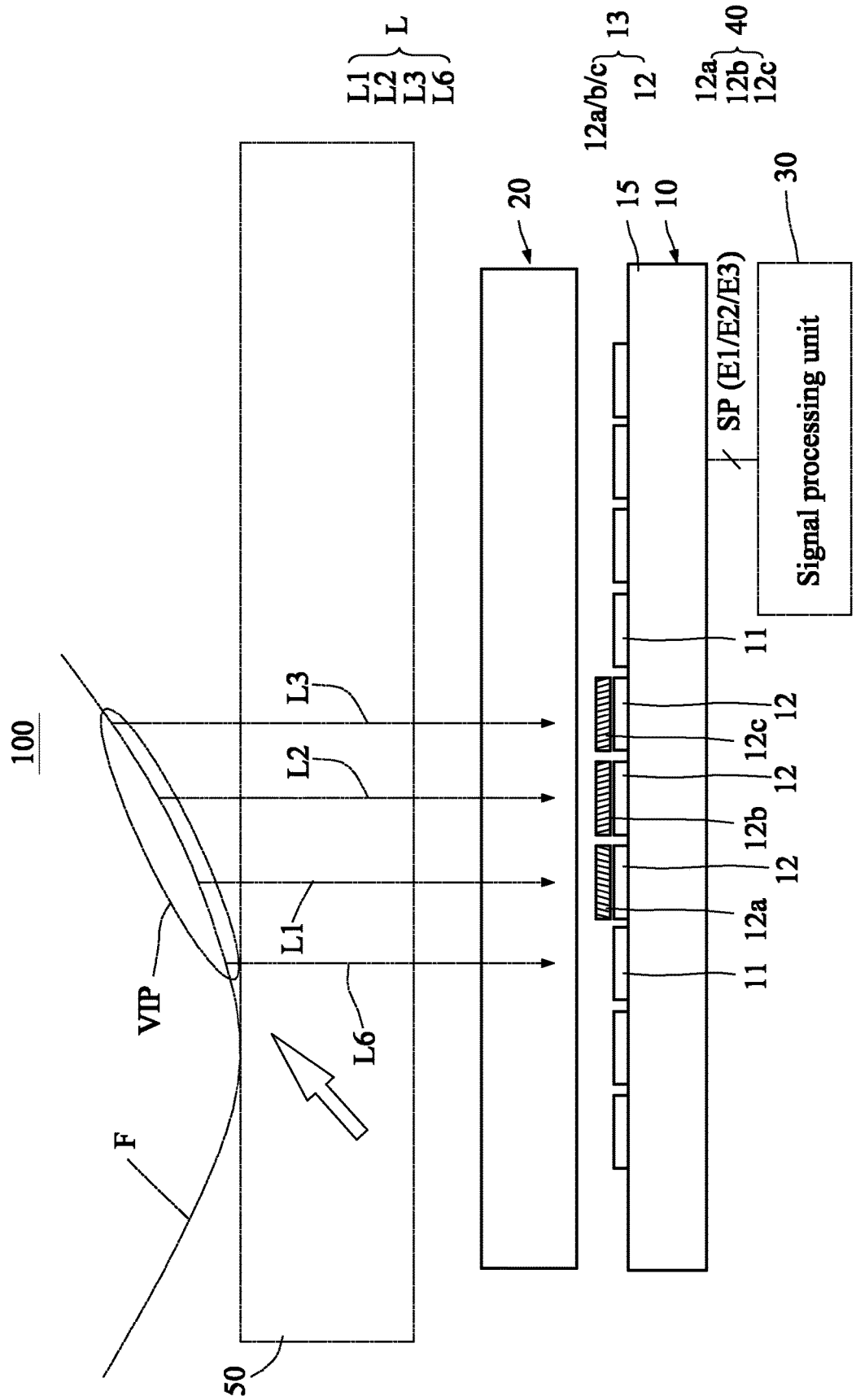
FIGS. 11 to 13 are schematically cross-sectional views showing partial systems of three examples of the integrated spectrum sensing devices of the preferred embodiment of this disclosure.
Figure 12:
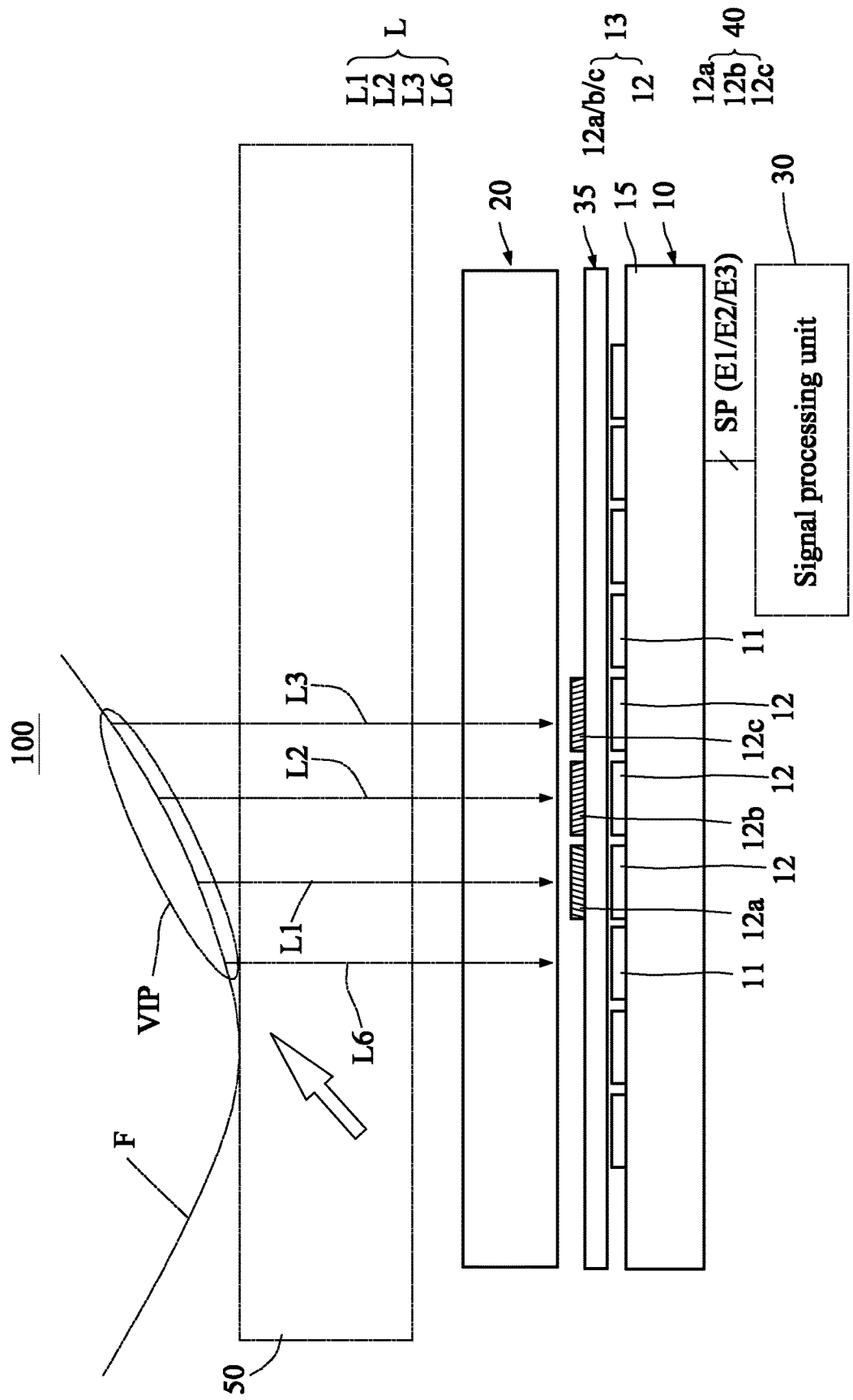
Figure 13:
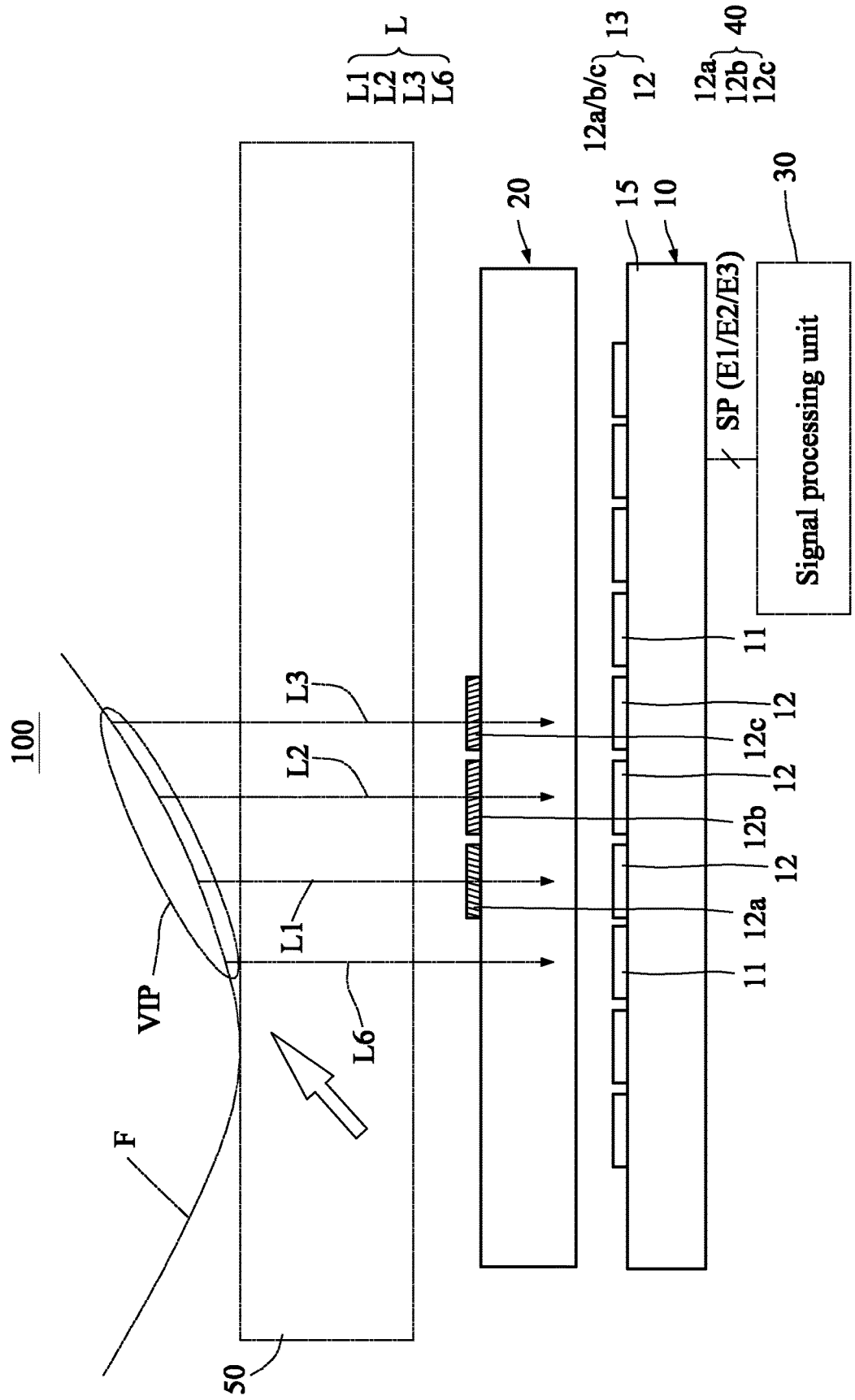

FIGS. 11 to 13 are schematically cross-sectional views showing partial systems of three examples of ISSDs 100 of the preferred embodiment of this disclosure. In FIG. 11, an ISSD 100 is disposed under a display 50 of a mobile phone, for example (such the ISSD 100 is also applicable to FIGS. 3A to 3D), senses the fingerprint of the finger F, and includes a fingerprint sensing array 10, an optical unit 20 and a spectrum separating module 40 (constituted by heterogeneous spectrum separating cells 12a, 12b and 12c). In one example, the display 50 provides the illumination light to illuminate the finger F, so that the finger F generates the light (e.g., reflected light) to be received by the spectrum detecting units 13. A sensing substrate 15 of the fingerprint sensing array 10 may be a semiconductor substrate forming a complementary metal oxide semiconductor (CMOS) optical image sensor, may also be another type of optical image sensor, such as an optical image sensor having thin-film transistors (TFTs) formed on a glass substrate, a sensor formed on a polymeric film, or any optical image sensor formed on any suitable substrate. The sensing substrate 15 has light sensing cells 11 and spectrum sensing cells 12 arranged in a two-dimensional array. In one example, the display 50 may provide the light to the finger F. In another example, a light emitting device (not shown) may be additionally provided to illuminate the finger.

The optical unit 20 is disposed above the sensing substrate 15. The spectrum separating module 40 works in conjunction with the optical unit 20 to separate the spectrums of the light rays L coming from the finger F and partially representative of the fingerprint of the finger F, and transmits the separated spectrums to the spectrum sensing cells 12, so that the spectrum sensing cells 12 obtain intensities, according to which the finger F may be judged as real or not (e.g., the intensity domain analysis pertaining to the measurement domain analysis). In this example, the finger F is judged as real according to one or multiple ratios of the intensities. In other examples, the finger F may be judged as real according to one or multiple differences or products of the mathematical combinations of the intensities, which may be used in statistics. If this technology is applied to the integrated real-finger spectrum sensing method, then the mathematical combinations (one or multiple ratios) of the intensities of the sets of heterogeneous spectrum data SP can be analyzed to judge whether the finger is real (the one or multiple ratios may be compared with the pre-detected data of the database to perform the judgement).

In FIG. 11, the spectrum separating module 40 includes heterogeneous spectrum separating cells 12a, 12b and 12c (or anti-spoofing spectrum separating cells) arranged in a neighboring manner (no other spectrum separating cell is present between neighboring two cells. The neighboring cells may be disposed side by side, or corner by corner), work in conjunction with the optical unit 20 to separate the spectrums of the light rays L including a first light ray L1, a second light ray L2 and a third light ray L3, and transmit the separated spectrums to three spectrum sensing cells 12, which obtain a first intensity E1, a second intensity E2 and a third intensity E3 of the intensities. Thus, the spectrum properties of the reflected light of the finger F can be obtained to judge the finger F as real according to the mathematical combinations (e.g., ratios (E1/E2) and (E2/E3)) of arbitrary two of the first to third intensities E1, E2 and E3. At this time, the first to third light rays L1 to L3 sensed by the three spectrum sensing cells 12 represent the virtual identical portion VIP of the finger F. In one example, the pitch between the ridges of the fingerprint ranges from about 400 to 500 µm, and the pitch between the spectrum sensing cells 12 ranges from about 10 to 20 µm, so that three neighboring spectrum sensing cells 12 actually need to measure the same portion of the fingerprint, the spectrum of this portion is referred to as that of the virtual identical portion or position, and the real physical meanings can be obtained. Because the VIP represents substantially the same depth information of the same point, the intensity cannot drift. This is because that the distance from the finger F to the three spectrum sensing cells 12 or the optical unit 20 is about 1,000 µm. When the difference between the transversal dimension and longitudinal dimension is relatively large, the three spectrum sensing cells 12 see almost the same portion. In addition, the optical unit 20 further transmits the normal light ray L6 coming from the finger F and partially representing the fingerprint to the corresponding light sensing cells 11 of the sensing substrate 15 to obtain the fingerprint image partially representing the fingerprint. The signals received by the spectrum sensing cell 12 can be used to judge the real finger, and may also be further compensated to obtain signals of several pixels of the fingerprint image.

Thus, the heterogeneous spectrum separating cells 12a, 12b and 12c adjacently cover the spectrum sensing cells 12, so that the spectrum sensing cells 12 corresponding to the heterogeneous spectrum separating cells 12a, 12b and 12c sense the spectrum distributions or variations outputted from the finger through the optical unit 20 and the heterogeneous spectrum separating cells 12a, 12b and 12c to obtain multiple sets of heterogeneous spectrum data SP.

In the example of FIG. 11, the heterogeneous spectrum separating cell 12a/12b/12c is the red/green/blue spectrum separating cell (the red spectrum is separated and passes through the heterogeneous spectrum separating cell 12a after the light ray impinges on the heterogeneous spectrum separating cell 12a), but this disclosure is not restricted thereto as long as the heterogeneous spectrum separating cells 12a, 12b and 12c allow light components with different wavelengths or spectrums to pass.

The optical unit 20 is also referred to as an optical engine disposed above the sensing substrate 15. The optical engine may be a lens-type optical engine (e.g., having two, three or multiple pieces of lenses), or an optical collimator engine (including a micro-lens array or an optical fiber (without a micro-lens)). The optical engine (e.g., the lens-type) may be separated from the sensing substrate 15 by a distance. Alternatively, the optical engine (e.g., the micro-lens array or the optical fiber) may be bonded to the sensing substrate 15 by the bonding method integrated with the manufacturing process, or by way of adhering and assembling. In addition, the optical unit 20 is disposed between the spectrum separating module 40 and the finger F. The heterogeneous spectrum separating cells 12a, 12b and 12c are respectively disposed on the three spectrum sensing cells 12. For example, the heterogeneous spectrum separating cells 12a, 12b and 12c are the optical films or bonding films corresponding to different wavelengths and being disposed on the three spectrum sensing cells 12 or the optical unit 20. Actually, two or more than two spectrums may function as separated or extracted spectrums of the anti-spoofing spectrum separating cells, which may fall within the visible light band (400 to 700 nm) or near-infrared light band (700 to 1,000 nm). If the bonding film is used, then the special alignment may not be needed. When the image processing is performed, an image without a finger can be captured, or a reference pattern can be captured, and the positions of the anti-spoofing spectrum separating cells and the corresponding light sensing cells may be found to serve as the reference for the subsequent fingerprint image capturing. It is worth noting that although three heterogeneous spectrum separating cells 12a, 12b and 12c are explained in the example, it is easily understood, from this disclosure, that two heterogeneous spectrum separating cells may also be used to achieve the effect of this embodiment.

The above-mentioned structure can be achieved by at least two neighboring pixels having at least two different spectrum separating configurations, wherein the first pixel receives the finger's reflected light through the first spectrum separating cell to obtain E1, the second pixel receives the finger's reflected light through the second spectrum separating cell to obtain E2, and the spectrum properties of the finger's reflected light can be obtained according to the ratio (E1/E2) and function as the basis for fake finger detection. Examples will be explained later.

It is worth noting that the ISSD 100 may further include the signal processing unit 30, which is electrically coupled to the light sensing cells 11 and spectrum sensing cells 12 (or electrically coupled to the spectrum detecting unit 13), and judges the finger F as real according to the intensities. The signal processing unit 30 may be an independent processor, or the CPU of an electronic device (e.g., mobile phone) working therewith. Because the light sensing cells 11 obtain the fingerprint image partially representing the fingerprint, the signal processing unit 30 processes the fingerprint image captured by the light sensing cells 11 only when judging the finger F as real. The heterogeneous spectrum separating cells 12a, 12b and 12c are disposed between the spectrum sensing cells 12 and the optical unit 20.

To summarize the embodiments of FIGS. 2 to 11, it is obtained that the signal processing unit 30 can perform measurement domain analysis according to multiple sets of heterogeneous spectrum data SP to judge whether the finger is real or not by performing, for example, one or multiple ones of the following mechanisms: (a) analyzing multiple sets of heterogeneous spectrum data SP in the spectrum variations in a time domain; (b) analyzing multiple sets of heterogeneous spectrum data SP in the spectrum variations in a spatial domain; and (c) analyzing relationships between multiple intensities of the sets of heterogeneous spectrum data SP (the intensity domain analysis of the sets of heterogeneous spectrum data SP). Only one of the mechanisms (a), (b) and (c) may be used to speed up the real-finger judgement; or two of the mechanisms (a), (b) and (c) can be used to possess the judgement speed and accuracy; or all of the mechanisms (a), (b) and (c) can be used to increase the judgement accuracy.

The example of FIG. 12 is similar to that of FIG. 11 except for the difference that the heterogeneous spectrum separating cells 12a, 12b and 12c are disposed on a transparent layer 35 above the sensing substrate 15 to facilitate the mass production and the cost reduction. It is worth noting that the anti-spoofing spectrum separating cells may be disposed on the upper surface or lower surface of the transparent layer 35, and the transparent layer 35 may be the light-permeable glass or another light-permeable medium.

A top-side spectrum separating configuration is provided in FIG. 13. Thus, the heterogeneous spectrum separating cells 12a, 12b and 12c of the spectrum separating module 40 are disposed between the optical unit 20 and the finger F. That is, the anti-spoofing spectrum separating cells are disposed on the upper surface of the optical unit 20 (e.g., the upper/lower surface of the micro-lens or the upper surface of the optical fiber collimator). Thus, the manufacturing cost of the optical unit 20 containing the spectrum separating cells 12a, 12b and 12c can be decreased.

Figure 14:
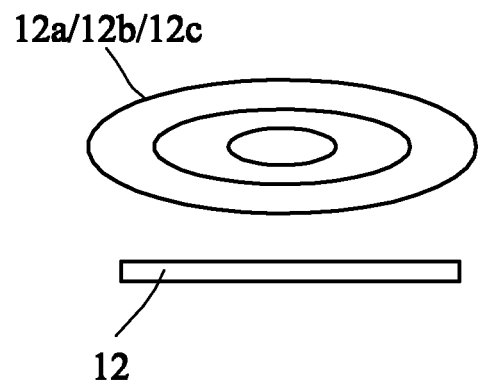
FIGS. 14 and 15 are schematic views showing two examples of anti-spoofing spectrum separating cells of the preferred embodiment of this disclosure.
Figure 15:
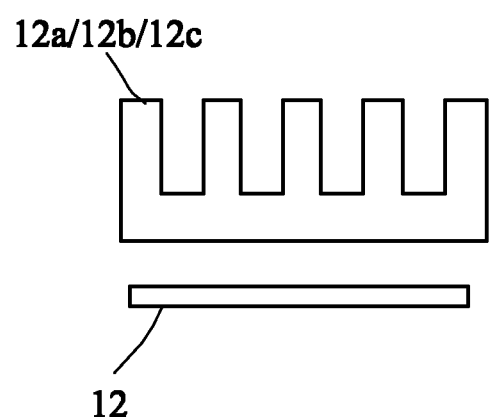

FIGS. 14 and 15 are schematic views showing two examples of anti-spoofing spectrum separating cells of the preferred embodiment of this disclosure. In FIG. 14, the heterogeneous spectrum separating cells 12a, 12b and/or 12c may be a surface plasmonic spectrum separator. In FIG. 15, the heterogeneous spectrum separating cells 12a, 12b and/or 12c may be a diffraction grating type spectrum separator.

Figure 16:
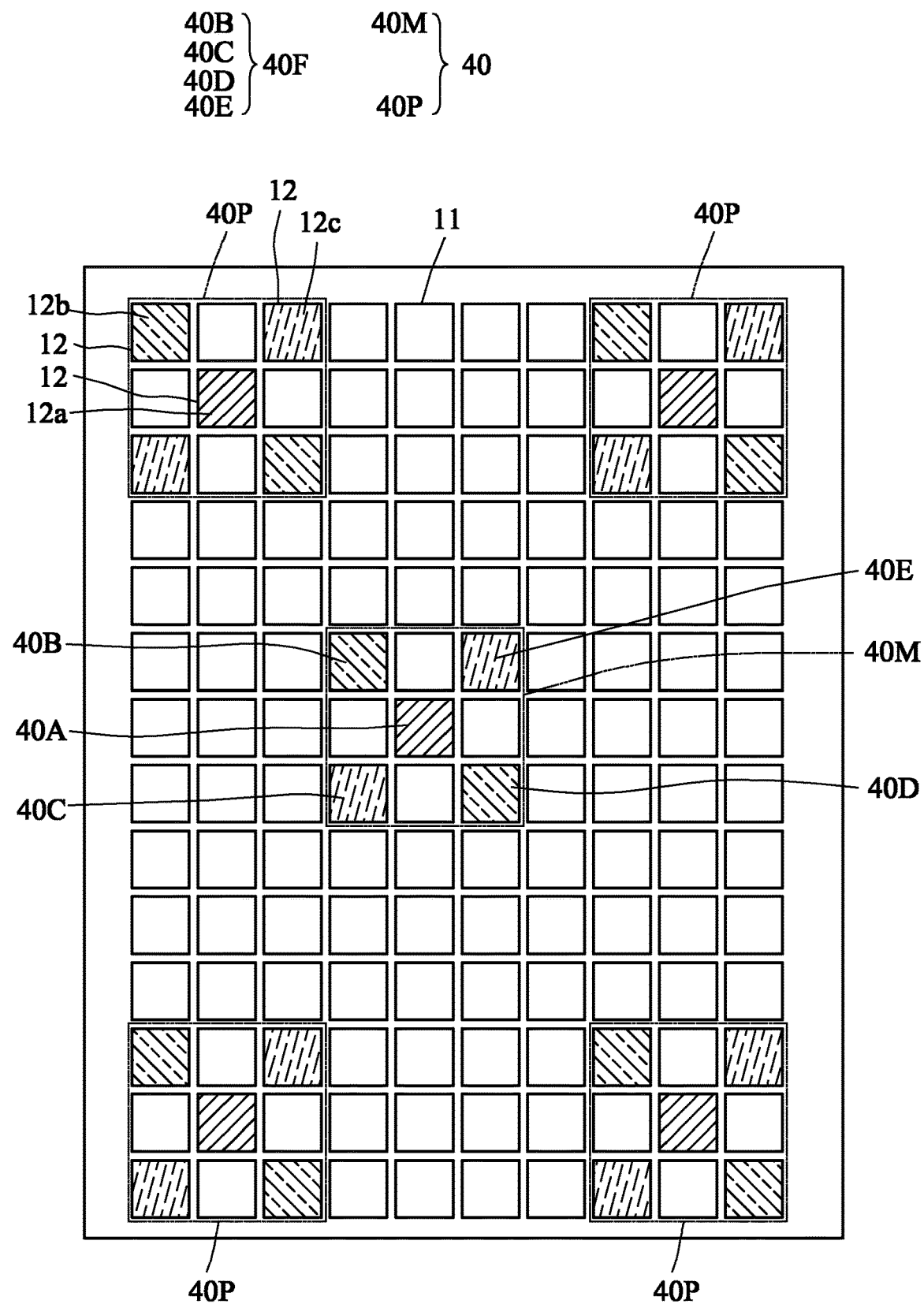
FIGS. 16 to 20 are top views showing examples of blocks of anti-spoofing spectrum separating cells.

FIGS. 16 to 20 are top views showing examples of blocks of anti-spoofing spectrum separating cells. In FIG. 16, the spectrum separating module 40 includes: a first block 40M having one or multiple ratios (central ratios) of these ratios; and one or multiple second blocks 40P being disposed beside the first block 40M and having one or multiple ratios (peripheral ratios) of these ratios. Thus, the finger F may be judged as real according to the one or multiple central ratios and the one or multiple peripheral ratios. The neighboring heterogeneous spectrum separating cells 12a, 12b and 12c of the spectrum separating module 40 allowing different wavelengths of light components to pass may be closely staggered. The first block 40M includes a middle anti-spoofing spectrum separating cell 40A and peripheral anti-spoofing spectrum separating cells 40F (40B-40E) disposed around the middle anti-spoofing spectrum separating cell 40A. In this example, four peripheral anti-spoofing spectrum separating cells 40F (40B-40E) are disposed at four corners of the middle anti-spoofing spectrum separating cell 40A. The light wavelengths separated by the middle anti-spoofing spectrum separating cell 40A differ from the light wavelengths separated by the peripheral anti-spoofing spectrum separating cells 40F (40B-40E). In this example, the peripheral anti-spoofing spectrum separating cells 40F (40B-40E) include anti-spoofing spectrum separating cells 40B (blue spectrum), 40C (red spectrum), 40D (blue spectrum) and 40E (red spectrum), and the middle anti-spoofing spectrum separating cell 40A is a green spectrum separating cell.

That is, the four peripheral anti-spoofing spectrum separating cells 40F (40B-40E) include first peripheral anti-spoofing spectrum separating cells 40B and 40D and second peripheral anti-spoofing spectrum separating cells 40C and 40E. The first peripheral anti-spoofing spectrum separating cells 40B and 40D neighbor upon two diagonal corners of the middle anti-spoofing spectrum separating cell 40A and generate the same first light wavelengths. The second peripheral anti-spoofing spectrum separating cells 40C and 40E neighbor upon the other two diagonal corner of the middle anti-spoofing spectrum separating cell 40A and generate the same second light wavelengths. However, the light wavelengths separated by the first peripheral anti-spoofing spectrum separating cells 40B and 40D differ from the light wavelengths separated by the second peripheral anti-spoofing spectrum separating cells 40C and 40E.

Figure 17:
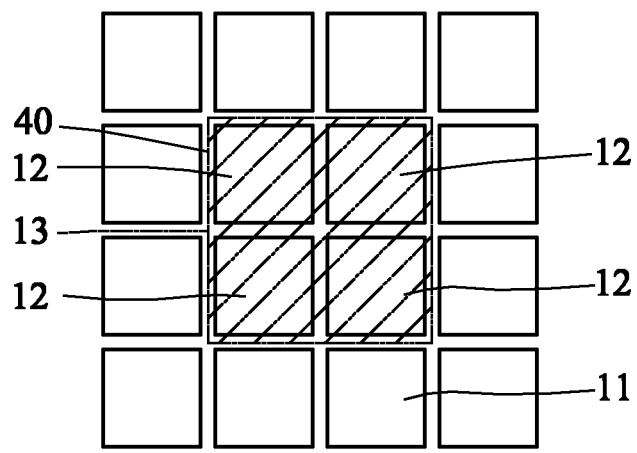
Figure 18:
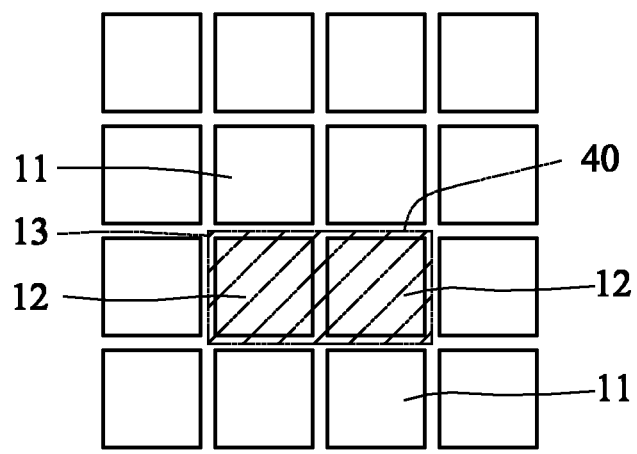

In FIGS. 17 and 18, multiple ones of the spectrum sensing cells 12 correspondingly receive the light from one anti-spoofing spectrum separating cell of the spectrum separating module 40. In FIG. 17, the one anti-spoofing spectrum separating cell of the spectrum separating module 40 covers four spectrum sensing cells 12. In FIG. 18, one anti-spoofing spectrum separating cell of the spectrum separating module 40 covers two spectrum sensing cells 12. Thus, the light sensing cells can obtain more information to increase the real-finger judging accuracy.

Figure 19:
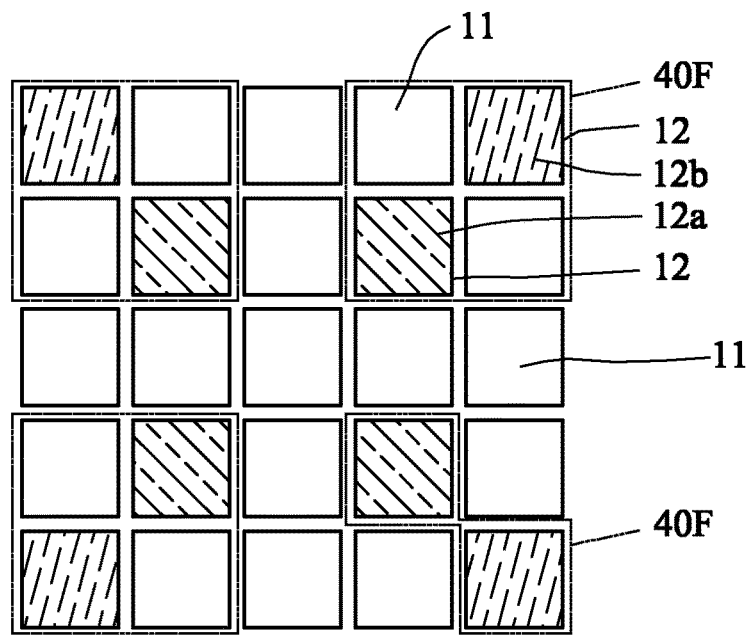
Figure 20:
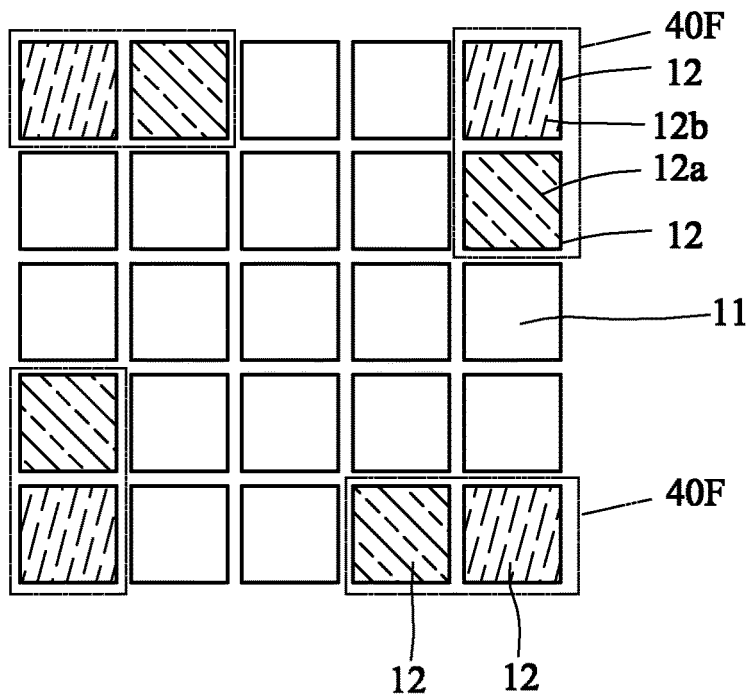

In FIG. 19, the diagonally neighboring heterogeneous spectrum separating cells 12a and 12b of the spectrum separating module 40 allowing different wavelengths of light components to pass are arranged in a direct neighboring manner. In FIG. 19, the peripheral anti-spoofing spectrum separating cell 40F may be regarded as an upper square region, or a region constituted by squares at two diagonal positions (e.g., the dashed line frame at the lower right corner). In FIG. 20, the neighboring heterogeneous spectrum separating cells 12a and 12b of the spectrum separating module 40 allowing different wavelengths of light components to pass are arranged in a direct transversal or longitudinal neighboring manner. In FIGS. 19 and 20, at least two neighboring pixels have at least two colors of spectrum separating configurations arranged in a closely spaced manner to assist the image interpolation upon image processing and to obtain the intensity of the reflected light of fingerprint's ridge or valley of the partial uniform region.

Figure 21:
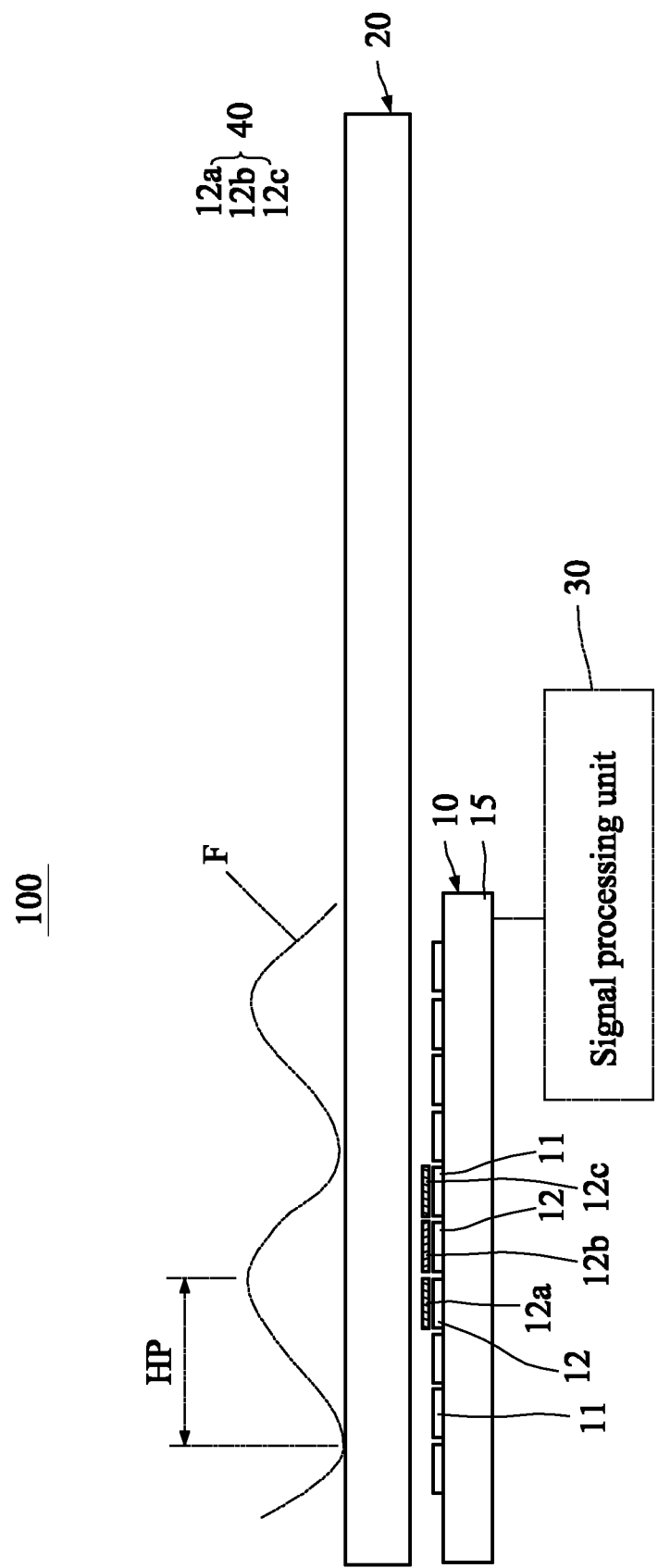
FIG. 21 is a schematic view showing design parameters of the fingerprint sensor of the preferred embodiment of this disclosure.

FIG. 21 is a schematic view showing design parameters of the fingerprint sensor of the preferred embodiment of this disclosure. In one single region of FIG. 21, the neighboring heterogeneous spectrum separating cells 12a and 12b of the spectrum separating module 40 allowing different wavelengths of light components to pass cover the actual fingerprint image having the range, which is associated with the distance between the neighboring ridge and valley of the finger F, and preferably smaller than one half of the minimum cycle of the fingerprint (2*HP), where HP denotes an half cycle, and 2*HP is equivalent to the distance between the neighboring ridges or valleys. So, the half cycle HP is equivalent to the distance between the neighboring ridge and valley, and ranges from 200 to 400 microns (μm). In one example, the neighboring heterogeneous spectrum separating cells 12a and 12b of the spectrum separating module 40 allowing different wavelengths of light components to pass cover the actual fingerprint image having a range smaller than 100 microns to obtain the more reasonable and easily distinguished ratio (E1/E2) or ratio (E2/E1). The range of the covered actual fingerprint image represents the range, in which the light sensing cells 11 can receive the light from the virtual identical portion VIP (FIG. 11) through the neighboring anti-spoofing spectrum separating cells.

Figure 22:
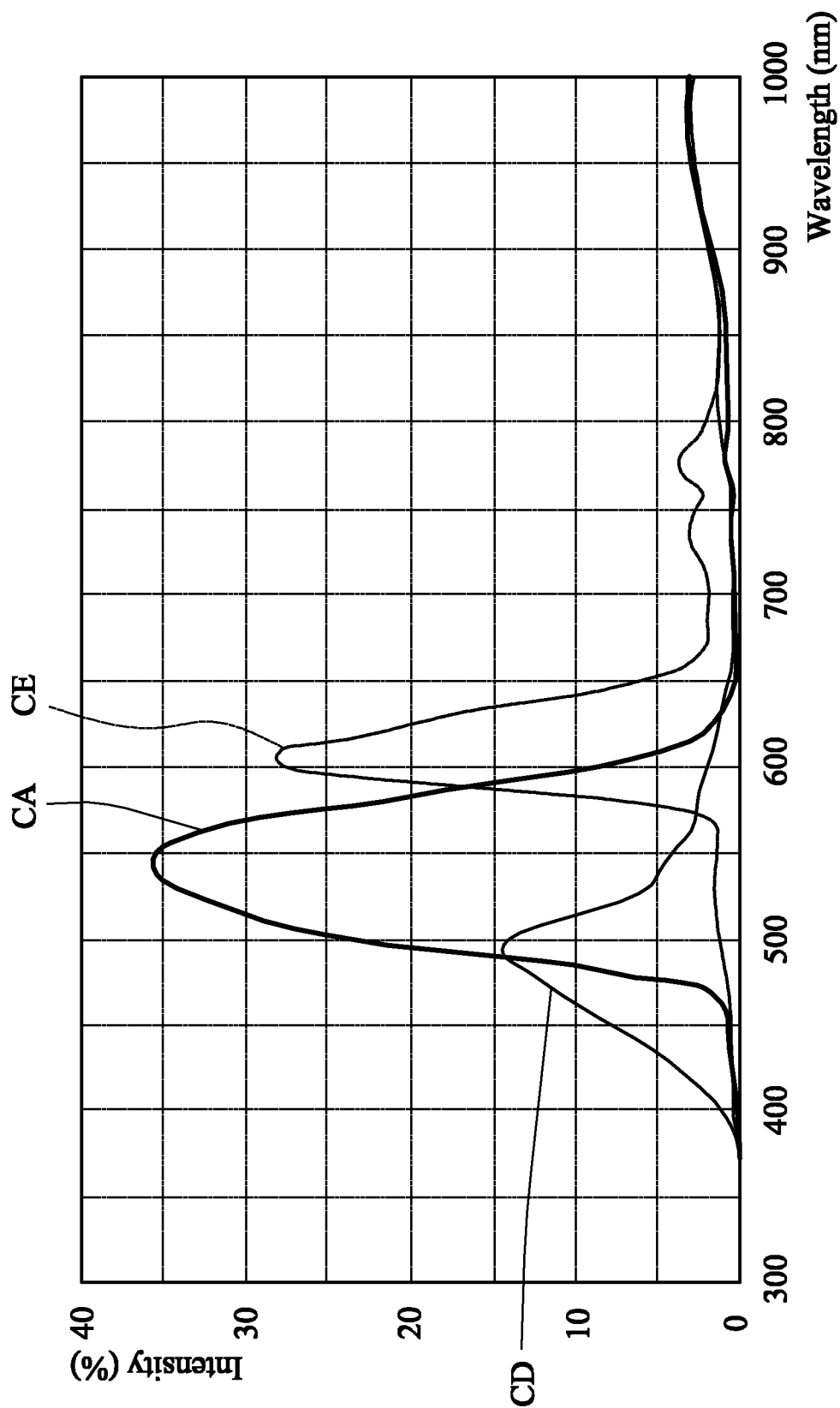
FIG. 22 shows a pixel response graph of the fingerprint sensor.

FIG. 22 shows a pixel response graph of the fingerprint sensor. In FIGS. 22 and 16, response curves CA, CD and CE respectively correspond to the middle anti-spoofing spectrum separating cell 40A (e.g., green spectrum separating cell), the first peripheral anti-spoofing spectrum separating cell 40D (e.g., blue spectrum separating cell) and the second peripheral anti-spoofing spectrum separating cell 40E (e.g., red spectrum separating cell), wherein the response curve CA has the highest peak intensity of about 36%; the response curve CD has the lowest peak intensity of about 14%; and the response curve CE has the moderate peak intensity of about 28%. At this time, the signal processing unit 30 can increase the sensitivity of one of the light sensing cells 11 (e.g., the light sensing cell corresponding to the first peripheral anti-spoofing spectrum separating cell 40D) to compensate one of the intensities. Alternatively, the signal processing unit 30 can adjust the integration time or gain of one or multiple ones of the light sensing cells 11 to compensate one of the intensities.

Figure 23:
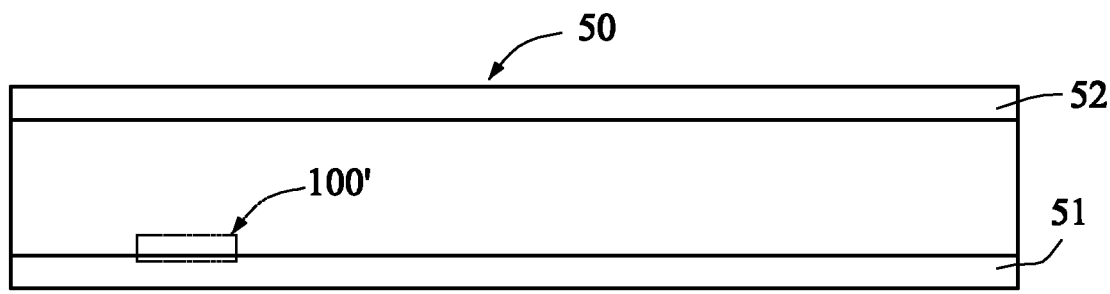
FIGS. 23 and 24 are schematic views showing two applications of fingerprint sensors.
Figure 24:
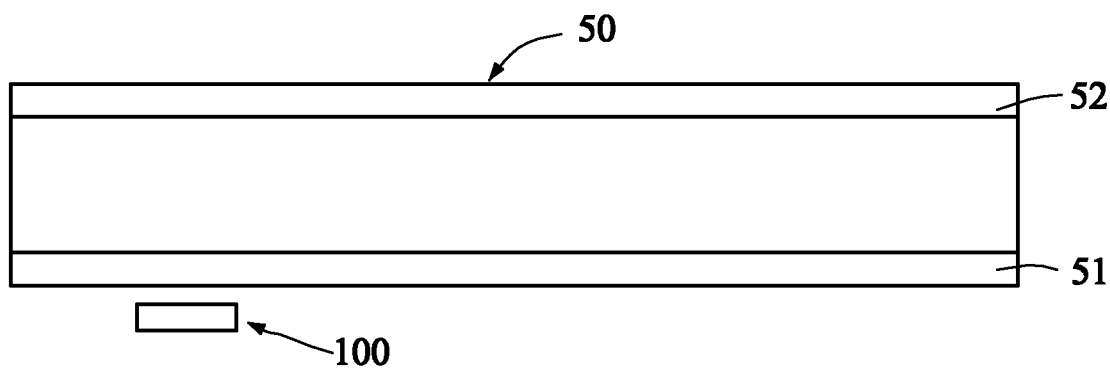

FIGS. 23 and 24 are schematic views showing two applications of fingerprint sensors. In FIG. 23, when the integrated spectrum sensing device is a TFT sensor, an ISSD 100' similar to the ISSD 100 and alternately integrated with display pixels (not shown) may become a liquid crystal display (LCD), an OLED display, a micro LED display or any other existing or future display having an in-cell sensor or a TFT sensor manufactured using the TFT manufacturing process. At this time, the sensing substrate 15 is one of two opposite light-permeable substrates 51 and 52 of the display 50 (the lower light-permeable substrate 51 in this figure, wherein the sensing substrate 15 may also be regarded as one portion of the light-permeable substrate 51). The material layer between the two light-permeable substrates 51 and 52 may be that contained in the OLED display or LCD. Although FIG. 23 is explained using the partial range of the ISSD 100' as an example, this disclosure is not restricted thereto. The ISSD 100' may also extend to cover the full range of the entire display 50, and become a full-screen fingerprint sensor. In FIG. 24, the ISSD 100 is an independent sensor, such as a TFT or CMOS sensor, disposed under the light-permeable substrate 51. It is worth noting that the display 50 in FIGS. 11 to 13 may be the LCD, OLED display, micro LED display or any other existing or future display for providing light to illuminate the finger.

Figure 25:
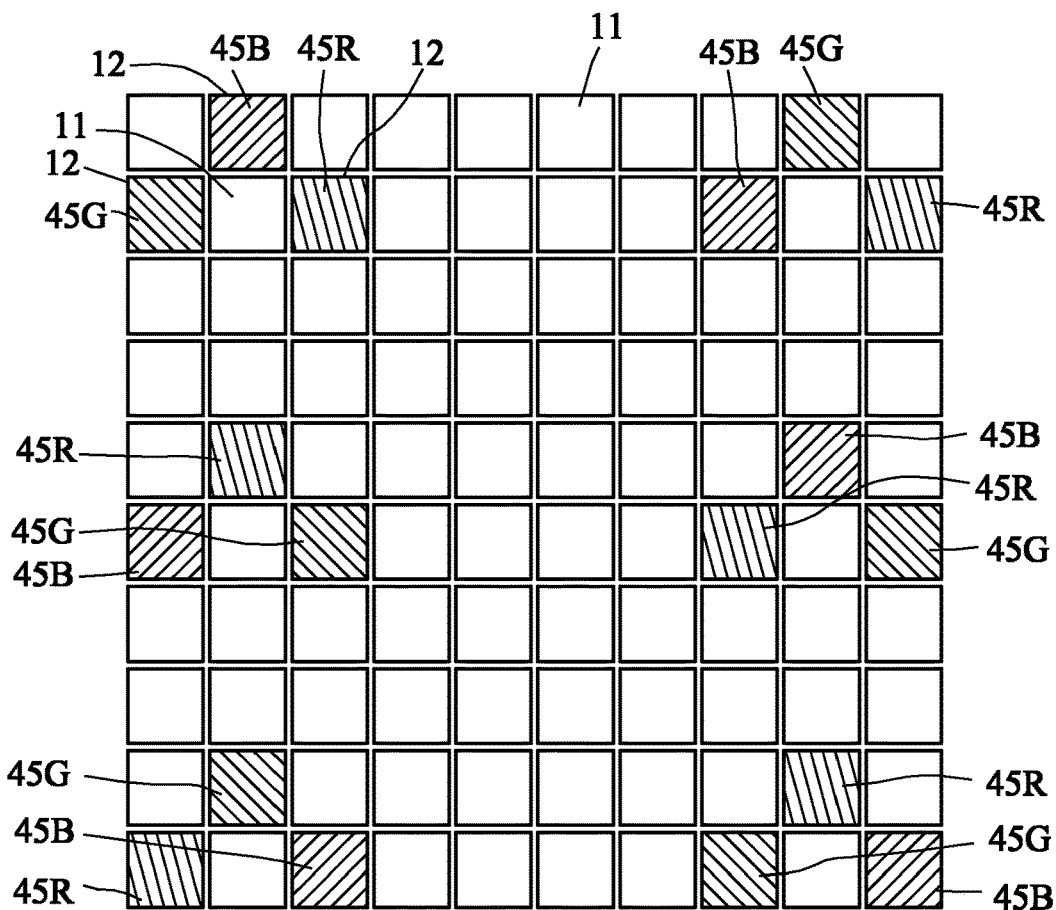
FIG. 25 is a schematic view showing the configuration of the anti-spoofing spectrum separating cell.

One example will be illustrated to prove that this disclosure can be implemented. FIG. 25 is a schematic view showing the configuration of the anti-spoofing spectrum separating cell. In FIG. 25, the neighboring red, green and blue anti-spoofing spectrum separating cells 45R, 45G and 45B constitute one set. The signal values of all light sensing cells 11 are listed in Tables 1 to 3, wherein the upper left corner is defined as the first column and first row, and the lower right corner is defined as the tenth column and tenth row. Table 1 lists the values corresponding to the real finger F1, and Tables 2 and 3 list the values corresponding to the two fake fingers F2 and F3.

TABLE 1

|        | Col. 1 | Col. 2 | Col. 3 | Col. 4 | Col. 5 | Col. 6 | Col. 7 | Col. 8 | Col. 9 | Col. 10 |
|--------|--------|--------|--------|--------|--------|--------|--------|--------|--------|---------|
| Row 1  | 133    | 60     | 230    | 348    | 0      | 0      | 219    | 52     | 155    | 245     |
| Row 2  | 20     | 43     | 75     | 302    | 279    | 106    | 275    | 0      | 122    | 106     |
| Row 3  | 41     | 311    | 0      | 57     | 112    | 162    | 300    | 130    | 149    | 224     |
| Row 4  | 103    | 326    | 100    | 0      | 68     | 0      | 321    | 331    | 93     | 235     |
| Row 5  | 0      | 75     | 216    | 0      | 285    | 0      | 36     | 201    | 0      | 341     |
| Row 6  | 0      | 24     | 163    | 68     | 275    | 310    | 0      | 46     | −67    | 135     |
| Row 7  | 223    | 90     | 209    | 0      | 191    | 381    | 0      | 284    | 0      | 142     |
| Row 8  | 345    | 43     | 272    | 49     | −69    | 118    | 0      | 310    | 391    | 163     |
| Row 9  | 53     | 28     | 291    | 339    | 71     | 324    | 0      | 20     | 101    | 42      |
| Row 10 | 69     | 224    | 9      | 287    | 27     | 170    | 263    | 23     | 106    | 0       |

As listed in Table 1, it is obtained that the averages (B, G, R) respectively corresponding to the blue, green and red anti-spoofing spectrum separating cells 45B, 45G and 45R can be written as B=11.5; G=87; and R=78. Thus, it is obtained that R/G=78/87=0.9; and B/G=11.5/87=0.13, where the red component C1 relative to green can be written as C1=α1*R/G=90, and the blue component C2 relative to green may be written as C2=α2*B/G=13, where α1 and α2 depend on different light sources. In this example, α1=100 and α2=100.

TABLE 2

| | Col. 1 | Col. 2 | Col. 3 | Col. 4 | Col. 5 | Col. 6 | Col. 7 | Col. 8 | Col. 9 | Col. 10 |
|---|---|---|---|---|---|---|---|---|---|---|
| Row 1 | 518 | 249 | 658 | 508 | 188 | 150 | 199 | 294 | 273 | 330 |
| Row 2 | 267 | 232 | 115 | 541 | 502 | 333 | 365 | 0 | 395 | 166 |
| Row 3 | 296 | 362 | 168 | 470 | 509 | 620 | 533 | 186 | 234 | 200 |
| Row 4 | 542 | 537 | 324 | 186 | 248 | 272 | 606 | 414 | 355 | 268 |
| Row 5 | 215 | 135 | 518 | 282 | 357 | 46 | 370 | 464 | 164 | 535 |
| Row 6 | 0 | 274 | 354 | 555 | 698 | 404 | 237 | 121 | 164 | 174 |
| Row 7 | 359 | 322 | 302 | 283 | 372 | 563 | 319 | 326 | 19 | 294 |
| Row 8 | 439 | 241 | 379 | 129 | 181 | 425 | 414 | 726 | 494 | 305 |
| Row 9 | 345 | 306 | 533 | 573 | 372 | 352 | 162 | 284 | 159 | 423 |
| Row 10 | 154 | 307 | 124 | 474 | 314 | 386 | 152 | 169 | 355 | 0 |

As listed in Table 2, it is obtained that the averages (B, G, R) respectively corresponding to the blue, green and red anti-spoofing spectrum separating cells 45B, 45G and 45R can be written as B=89; G=257; and R=141. Thus, it is obtained that R/G=141/257=0.54; and B/G=89/257=0.35, where the red component C1 relative to green can be written as C1=α1*R/G=54, and the blue component C2 relative to green may be written as C2=α2*B/G=35, where α1 and α2 depend on different light sources. In this example, α1=100 and α2=100.

TABLE 3

| | Col. 1 | Col. 2 | Col. 3 | Col. 4 | Col. 5 | Col. 6 | Col. 7 | Col. 8 | Col. 9 | Col. 10 |
|---|---|---|---|---|---|---|---|---|---|---|
| Row 1 | 450 | 90 | 547 | 627 | 254 | 447 | 263 | 553 | 389 | 513 |
| Row 2 | 394 | 217 | 153 | 669 | 407 | 515 | 382 | 0 | 353 | 136 |
| Row 3 | 667 | 349 | 360 | 360 | 419 | 552 | 751 | 219 | 569 | 370 |
| Row 4 | 482 | 579 | 433 | 334 | 298 | 482 | 553 | 475 | 635 | 385 |
| Row 5 | 324 | 193 | 429 | 640 | 463 | 224 | 353 | 449 | 249 | 654 |
| Row 6 | 0 | 323 | 319 | 535 | 788 | 335 | 496 | 125 | 340 | 305 |
| Row 7 | 309 | 487 | 439 | 449 | 551 | 502 | 585 | 659 | 156 | 408 |
| Row 8 | 513 | 518 | 542 | 330 | 227 | 415 | 542 | 765 | 442 | 635 |
| Row 9 | 330 | 304 | 688 | 454 | 491 | 605 | 273 | 242 | 192 | 684 |
| Row 10 | 174 | 368 | 86 | 428 | 532 | 588 | 286 | 392 | 465 | 9 |

As listed in Table 3, it is obtained that the averages (B, G, R) respectively corresponding to the blue, green and red anti-spoofing spectrum separating cells 45B, 45G and 45R can be written as B=72; G=350; and R=162. Thus, it is obtained that R/G=162/350=0.462; and B/G=72/350=0.2, where the red component C1 relative to green can be written as C1=α1*R/G=46, and the blue component C2 relative to green may be written as C2=α2*B/G=20, where α1 and α2 depend on different light sources. In this example, α1=100 and α2=100.

Figure 26:
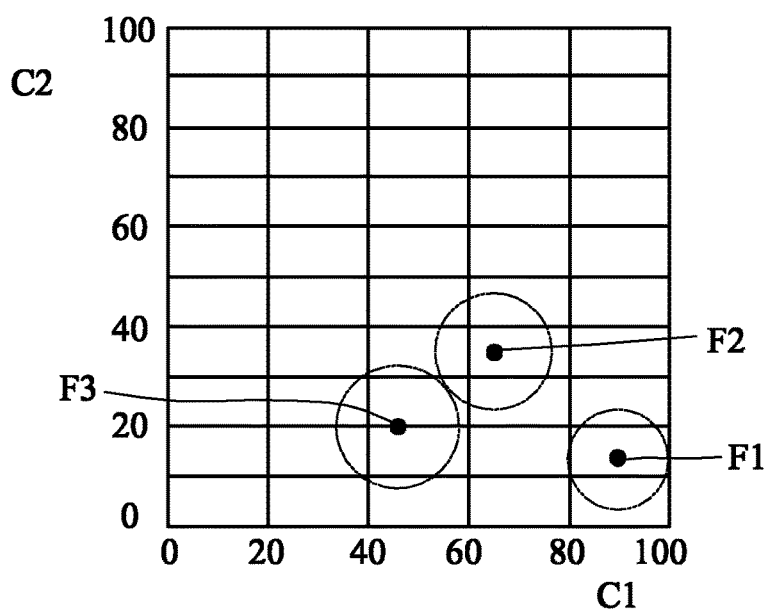
FIG. 26 is a relation chart showing C1 and C2 of sensing results of three fingers.

FIG. 26 is a relation chart showing C1 and C2 of sensing results of three fingers. In FIG. 26, the distribution range of the real finger F1 falls at the lower right corner (i.e., C1 is high and C2 is low). Because the real finger F1 has veins, the red component relative to green is high, and the blue component relative to green is low. The fake fingers F2 and F3 have no vein, so C1 is low and C2 is high. Thus, the real finger can be judged according to the ratio(s) of the intensities. Of course, the associated database can be created according to several states and test data of the fingers, wherein comparisons of C1 and C2 with the database can be made or even in conjunction with the artificial intelligence training to perform the real-finger judgement.

Figure 27:
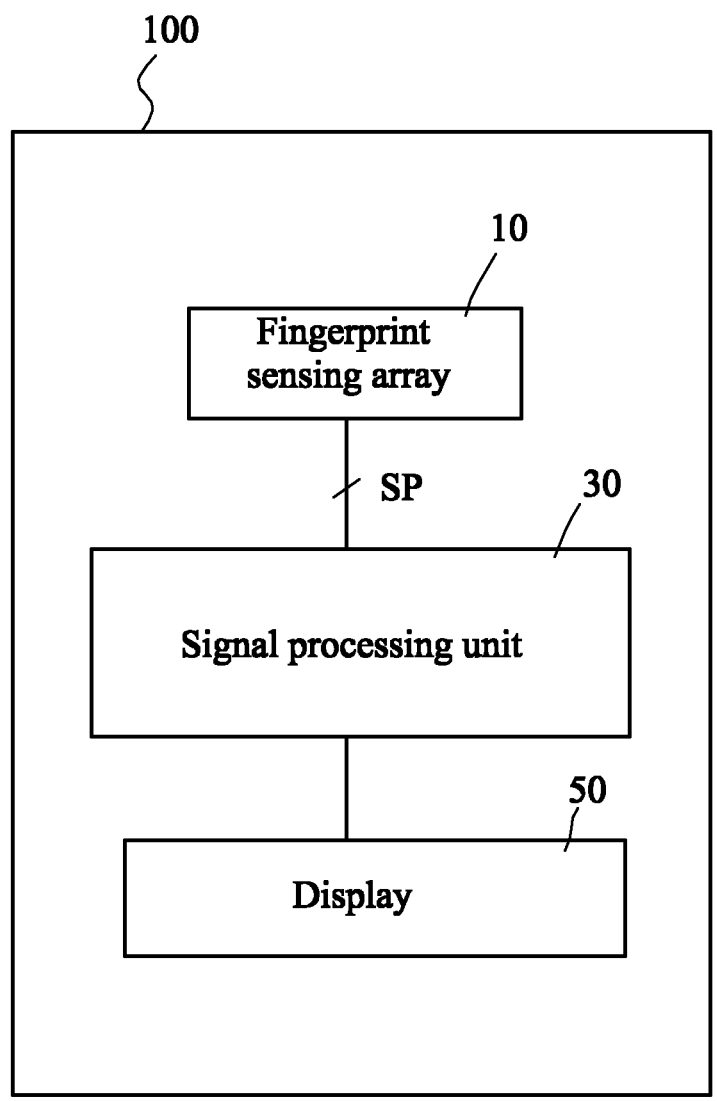
FIG. 27 is a schematic block diagram showing another example of the integrated spectrum sensing device.

FIG. 27 is a schematic block diagram showing another example of the integrated spectrum sensing device. In FIG. 27, the ISSD 100 is a mobile device (e.g., mobile phone, tablet computer or the like). Thus, the signal processing unit 30 functions as a CPU of the mobile device, and performs control and signal processing on the fingerprint sensing array 10 and display 50. In this condition, the cost of the overall system can be decreased using the CPU of the mobile device with the powerful calculation function to perform signal processing and judgement.

With the above-mentioned integrated spectrum sensing device of the embodiments, neighboring light sensing cells are used in conjunction with different spectrum separating cells to obtain different intensities, and whether the finger is real is judged according to one or multiple ratios of these intensities. The simple optical coating treatment for the spectrum separating cells is utilized so that the manufacturing cost needs not to be significantly increased and that the anti-spoofing detection of the finger can be achieved. Also, the problem that the interested party intends to pass fingerprint verification using the fake finger can be effectively solved.

It is worth noting that all the above embodiments can be combined, replaced or modified interactively as appropriate to provide the real-finger judgement accuracy, speed and stability.

While this disclosure has been described by way of examples and in terms of preferred embodiments, it is to be understood that this disclosure is not limited thereto. To the contrary, it is intended to cover various modifications. Therefore, the scope of the appended claims should be accorded the broadest interpretation so as to encompass all such modifications.

What is claimed is:
1. An integrated spectrum sensing device, comprising:
an optical unit;

a fingerprint sensing array being optically coupled to the optical unit and comprising multiple spectrum detecting units receiving light from a finger through the optical unit to detect spectrum distributions or spectrum variations outputted from the finger to obtain multiple sets of heterogeneous spectrum data; and a signal processing unit being electrically coupled to the spectrum detecting units and performing measurement domain analysis according to the sets of heterogeneous spectrum data to judge whether the finger is real by one or multiple ones of:

analyzing color variations of the sets of heterogeneous spectrum data representative of a virtual identical portion of the finger on a time axis to perform dynamic spectrum verification to determine whether a skin color of the virtual identical portion of the finger changes with time;

analyzing whether level variations of the sets of heterogeneous spectrum data at a wavelength ranging from 380 nm to 580 nm reach a predetermined level; and analyzing whether position variations of the sets of heterogeneous spectrum data in a CIE 1931 color space reach a predetermined offset.

2. The integrated spectrum sensing device according to claim 1, wherein the measurement domain analysis comprises: analyzing the spectrum variations of the sets of heterogeneous spectrum data in a time domain, in which spectrums of the sets of heterogeneous spectrum data representative of the virtual identical portion of the finger change with time when the finger performs a touch changing with time, according to a graph of time versus a level corresponding to spectrum intensity information.

3. The integrated spectrum sensing device according to claim 2, wherein the measurement domain analysis comprises: analyzing the spectrum variations of the sets of heterogeneous spectrum data in a spatial domain, in which local images corresponding to the sets of heterogeneous spectrum data are obtained at different positions in a same time period.

4. The integrated spectrum sensing device according to claim 2, wherein the measurement domain analysis comprises: analyzing relationships between multiple intensities of the sets of heterogeneous spectrum data.

5. The integrated spectrum sensing device according to claim 2, wherein the measurement domain analysis comprises: analyzing the spectrum variations of the sets of heterogeneous spectrum data in a spatial domain, in which local images corresponding to the sets of heterogeneous spectrum data are obtained at different positions in a same time period; and analyzing relationships between multiple intensities of the sets of heterogeneous spectrum data.

6. The integrated spectrum sensing device according to claim 1, wherein the measurement domain analysis comprises: analyzing the spectrum variations of the sets of heterogeneous spectrum data in a spatial domain, in which local images corresponding to the sets of heterogeneous spectrum data are obtained at different positions in a same time period.

7. The integrated spectrum sensing device according to claim 1, wherein the measurement domain analysis comprises: analyzing relationships between multiple intensities of the sets of heterogeneous spectrum data.

8. The integrated spectrum sensing device according to claim 1, wherein the measurement domain analysis comprises: analyzing the spectrum variations of the sets of heterogeneous spectrum data in a spatial domain, in which local images corresponding to the sets of heterogeneous spectrum data are obtained at different positions in a same time period; and analyzing relationships between multiple intensities of the sets of heterogeneous spectrum data.

9. The integrated spectrum sensing device according to claim 1, wherein the signal processing unit comprises a sensing region selector being electrically coupled to the fingerprint sensing array, and selecting a sensing region of the fingerprint sensing array according to a touch event signal to enable the fingerprint sensing array to generate the sets of heterogeneous spectrum data corresponding to the sensing region.

10. The integrated spectrum sensing device according to claim 1, further comprising a display being electrically coupled to the signal processing unit and providing illumination light to illuminate the finger, so that the finger outputs the light received by the spectrum detecting units, wherein the fingerprint sensing array is disposed under the display.

11. The integrated spectrum sensing device according to claim 10, wherein the display is a LCD, an OLED display or a micro LED display.

12. The integrated spectrum sensing device according to claim 10 being a mobile device, wherein the signal processing unit functions as a CPU of the mobile device, and performs controlling and signal processing on the fingerprint sensing array and the display.

13. The integrated spectrum sensing device according to claim 1 being electrically coupled to a host, wherein the signal processing unit is electrically coupled to a CPU of the host, and the CPU is electrically coupled to a display of the host and controls operations of the display and the signal processing unit.

14. The integrated spectrum sensing device according to claim 1, wherein the fingerprint sensing array senses a sensing region at a first time and a second time to obtain the sets of heterogeneous spectrum data, and the signal processing unit analyzes the spectrum variations of the sets of heterogeneous spectrum data at the first time and the second time to judge whether the finger is real, wherein a first pressure of the finger directly or indirectly contacting the fingerprint sensing array at the first time in a starting period or an ending period of a touch event is lower than a second pressure of the finger directly or indirectly contacting the fingerprint sensing array at the second time in a stable touching period of the touch event.

15. The integrated spectrum sensing device according to claim 1, wherein the fingerprint sensing array senses different positions of a sensing region to obtain the sets of heterogeneous spectrum data, and the signal processing unit analyzes the spectrum variations of the sets of heterogeneous spectrum data at the different positions to judge whether the finger is real.

16. The integrated spectrum sensing device according to claim 1, wherein the fingerprint sensing array senses a sensing region at a first time and a second time to obtain the sets of heterogeneous spectrum data, and the signal processing unit analyzes the spectrum variations of the sets of heterogeneous spectrum data at the first time and the second time to judge whether the finger is real, wherein a first pressure of the finger directly or indirectly contacting the fingerprint sensing array at the first time in a starting period or an ending period of a touch event is lower than a second pressure of the finger directly or indirectly contacting the fingerprint sensing array at the second time in a stable touching period of the touch event; and the signal processing unit analyzes the spectrum variations of the sets of heterogeneous spectrum data corresponding to one or both of the first time and the second time at different positions to judge whether the finger is real.

17. The integrated spectrum sensing device according to claim 1, wherein the fingerprint sensing array further comprises multiple light sensing cells, the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense the finger through the optical unit and the heterogeneous spectrum separating cells, and that the light sensing cells sense a fingerprint of the finger through the optical unit to obtain a fingerprint image.

18. The integrated spectrum sensing device according to claim 1, wherein the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense the finger through the optical unit and the heterogeneous spectrum separating cells, wherein each of the heterogeneous spectrum separating cells is a surface plasmonic spectrum separator or a diffraction grating spectrum separator.

19. The integrated spectrum sensing device according to claim 1, wherein intensities of the sets of heterogeneous spectrum data comprise a first intensity and a second intensity, and it is judged whether the finger is real according to a ratio of the first intensity to the second intensity, wherein the first intensity and the second intensity represent intensities of heterogeneous spectrums of the virtual identical portion of the finger.

20. The integrated spectrum sensing device according to claim 19, wherein the intensities further comprise a third intensity, and it is judged whether the finger is real according to the ratio of the first intensity to the second intensity and a ratio of the second intensity to the third intensity.

21. The integrated spectrum sensing device according to claim 1, wherein the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense the finger through the optical unit and the heterogeneous spectrum separating cells, wherein multiple ones of the spectrum sensing cells correspondingly receive light from one of the heterogeneous spectrum separating cells.

22. The integrated spectrum sensing device according to claim 1, wherein the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense the finger through the optical unit and the heterogeneous spectrum separating cells, wherein neighboring two of the heterogeneous spectrum separating cells are arranged in a direct neighboring manner in a diagonal direction, a transversal direction or a longitudinal direction.

23. The integrated spectrum sensing device according to claim 1, wherein the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense a fingerprint of the finger through the optical unit and the heterogeneous spectrum separating cells, wherein neighboring two of the heterogeneous spectrum separating cells cover an actual fingerprint image with a range smaller than one half of a minimum cycle of the fingerprint.

24. The integrated spectrum sensing device according to claim 1, wherein the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense the finger through the optical unit and the heterogeneous spectrum separating cells, wherein neighboring two of the heterogeneous spectrum separating cells cover an actual fingerprint image with a range smaller than 100 microns.

25. The integrated spectrum sensing device according to claim 24, wherein the signal processing unit increases a sensitivity, an integration time or a gain of one of the spectrum sensing cells corresponding to the heterogeneous spectrum separating cells to compensate one of multiple intensities of the sets of heterogeneous spectrum data.

26. An integrated spectrum sensing device, comprising:
   an optical unit;
   a fingerprint sensing array being optically coupled to the optical unit and comprising multiple spectrum detecting units receiving light from a finger through the optical unit to detect spectrum distributions or spectrum variations outputted from the finger to obtain multiple sets of heterogeneous spectrum data; and
   a signal processing unit being electrically coupled to the spectrum detecting units and performing measurement domain analysis according to the sets of heterogeneous spectrum data to judge whether the finger is real, wherein the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense the finger through the optical unit and the heterogeneous spectrum separating cells, wherein the heterogeneous spectrum separating cells at least define a first block and one or multiple second blocks disposed beside the first block, the first block has one or multiple central ratios, and the one or multiple second blocks have one or multiple peripheral ratios, so that it is judged whether the finger is real according to the one or multiple central ratios and the one or multiple peripheral ratios.

27. The integrated spectrum sensing device according to claim 26, wherein the first block comprises:
   a middle anti-spoofing spectrum separating cell; and
   multiple peripheral anti-spoofing spectrum separating cells disposed around the middle anti-spoofing spectrum separating cell, wherein light wavelengths separated by the middle anti-spoofing spectrum separating cell differ from light wavelengths separated by the peripheral anti-spoofing spectrum separating cells.

28. The integrated spectrum sensing device according to claim 26, wherein the first block comprises:
   a middle anti-spoofing spectrum separating cell; and
   four peripheral anti-spoofing spectrum separating cells disposed around four corners of the middle anti-spoofing spectrum separating cell, wherein light wavelengths separated by the middle anti-spoofing spectrum separating cell differ from light wavelengths separated by the four peripheral anti-spoofing spectrum separating cells.

29. The integrated spectrum sensing device according to claim 28, wherein the four peripheral anti-spoofing spectrum separating cells comprise multiple first peripheral anti-spoofing spectrum separating cells and multiple second peripheral anti-spoofing spectrum separating cells, the first peripheral anti-spoofing spectrum separating cells neighbor upon two diagonal corners of the middle anti-spoofing spectrum separating cell and generate a same first light wavelength, and the second peripheral anti-spoofing spectrum separating cells neighbor upon the other two diagonal corners of the middle anti-spoofing spectrum separating cell and generate a same second light wavelength, wherein the first light wavelengths separated by the first peripheral anti-spoofing spectrum separating cells differ from the second light wavelengths separated by the second peripheral anti-spoofing spectrum separating cells.

30. An integrated real-finger spectrum sensing method, comprising steps of:
(a) using multiple spectrum detecting units of a fingerprint sensing array to sense spectrum distributions or spectrum variations outputted from a finger through an optical unit to obtain multiple sets of heterogeneous spectrum data, wherein the optical unit is optically coupled to the spectrum detecting units; and
(b) performing measurement domain analysis according to the sets of heterogeneous spectrum data to judge whether the finger is real by one or multiple ones of:
analyzing color variations of the sets of heterogeneous spectrum data representative of a virtual identical portion of the finger on a time axis to perform dynamic spectrum verification to determine whether a skin color of the virtual identical portion of the finger changes with time;
analyzing whether level variations of the sets of heterogeneous spectrum data at a wavelength ranging from 380 nm to 580 nm reach a predetermined level; and
analyzing whether position variations of the sets of heterogeneous spectrum data in a CIE 1931 color space reach a predetermined offset.

31. The integrated real-finger spectrum sensing method according to claim 30, wherein the measurement domain analysis comprises: analyzing the spectrum variations of the sets of heterogeneous spectrum data in a time domain, in which spectrums of the sets of heterogeneous spectrum data representative of the virtual identical portion of the finger change with time when the finger performs a touch changing with time, according to a graph of time versus a level corresponding to spectrum intensity information.

32. The integrated real-finger spectrum sensing method according to claim 31, wherein the measurement domain analysis comprises: analyzing the spectrum variations of the sets of heterogeneous spectrum data in a spatial domain, in which local images corresponding to the sets of heterogeneous spectrum data are obtained at different positions in a same time period.

33. The integrated real-finger spectrum sensing method according to claim 31, wherein the measurement domain analysis comprises: analyzing relationships between multiple intensities of the sets of heterogeneous spectrum data.

34. The integrated real-finger spectrum sensing method according to claim 31, wherein the measurement domain analysis comprises: analyzing the spectrum variations of the sets of heterogeneous spectrum data in a spatial domain, in which local images corresponding to the sets of heterogeneous spectrum data are obtained at different positions in a same time period; and analyzing relationships between multiple intensities of the sets of heterogeneous spectrum data.

35. The integrated real-finger spectrum sensing method according to claim 30, wherein the measurement domain analysis comprises: analyzing the spectrum variations of the sets of heterogeneous spectrum data in a spatial domain, in which local images corresponding to the sets of heterogeneous spectrum data are obtained at different positions in a same time period.

36. The integrated real-finger spectrum sensing method according to claim 30, wherein the measurement domain analysis comprises: analyzing relationships between multiple intensities of the sets of heterogeneous spectrum data.

37. The integrated real-finger spectrum sensing method according to claim 30, wherein the measurement domain analysis comprises: analyzing the spectrum variations of the sets of heterogeneous spectrum data in a spatial domain, in which local images corresponding to the sets of heterogeneous spectrum data are obtained at different positions in a same time period; and analyzing relationships between multiple intensities of the sets of heterogeneous spectrum data.

38. The integrated real-finger spectrum sensing method according to claim 30, further comprising steps of:
receiving a touch event signal and selecting a sensing region according to the touch event signal of the fingerprint sensing array to enable the fingerprint sensing array to generate the sets of heterogeneous spectrum data corresponding to the sensing region.

39. The integrated real-finger spectrum sensing method according to claim 30, wherein in the step (a), the fingerprint sensing array is utilized to sense a sensing region at a first time and a second time after the first time to obtain the sets of heterogeneous spectrum data, wherein in the step (b), the spectrum variations of the sets of heterogeneous spectrum data at the first time and the second time are analyzed to judge whether the finger is real, wherein a first pressure of the finger directly or indirectly contacting the fingerprint sensing array at the first time in a starting period or an ending period of a touch event is lower than a second pressure of the finger directly or indirectly contacting the fingerprint sensing array at the second time in a stable touching period of the touch event.

40. The integrated real-finger spectrum sensing method according to claim 30, wherein in the step (a), the fingerprint sensing array is utilized to sense different positions of a sensing region to obtain the sets of heterogeneous spectrum data, wherein in the step (b), the spectrum variations of the sets of heterogeneous spectrum data at the different positions are analyzed to judge whether the finger is real.

41. The integrated real-finger spectrum sensing method according to claim 30, wherein:
in the step (a), the fingerprint sensing array is utilized to sense a sensing region at a first time and a second time to obtain the sets of heterogeneous spectrum data; and
in the step (b), the spectrum variations of the sets of heterogeneous spectrum data at the first time and the second time are analyzed to judge whether the finger is real, wherein a first pressure of the finger directly or indirectly contacting the fingerprint sensing array at the first time in a starting period or an ending period of a touch event is lower than a second pressure of the finger directly or indirectly contacting the fingerprint sensing array at the second time in a stable touching period of the touch event; and the spectrum variations of the sets of heterogeneous spectrum data corresponding to one or both of the first time and the second time at different positions are analyzed to judge whether the finger is real.

42. The integrated real-finger spectrum sensing method according to claim 30, wherein in the step (b), one or multiple mathematical combinations of multiple intensities of the sets of heterogeneous spectrum data are analyzed to judge whether the finger is real.

43. The integrated real-finger spectrum sensing method according to claim 30, wherein in the step (b), one or multiple ratios of multiple intensities of the sets of heterogeneous spectrum data are analyzed to judge whether the finger is real.

44. An integrated real-finger spectrum sensing method, comprising steps of:
(a) using multiple spectrum detecting units of a fingerprint sensing array to sense spectrum distributions or spectrum variations outputted from a finger through an optical unit to obtain multiple sets of heterogeneous spectrum data, wherein the optical unit is optically coupled to the spectrum detecting units, and the spectrum detecting units comprise multiple spectrum sensing cells and multiple neighboring heterogeneous spectrum separating cells covering the spectrum sensing cells, so that the spectrum sensing cells corresponding to the heterogeneous spectrum separating cells sense the finger through the optical unit and the heterogeneous spectrum separating cells, wherein the heterogeneous spectrum separating cells at least define a first block and one or multiple second blocks disposed beside the first block, the first block has one or multiple central ratios, and the one or multiple second blocks have one or multiple peripheral ratios; and
(b) performing measurement domain analysis according to the sets of heterogeneous spectrum data to judge whether the finger is real according to the one or multiple central ratios and the one or multiple peripheral ratios.

* * * * *